(12) United States Patent
Ragini et al.

(10) Patent No.: US 8,039,123 B2
(45) Date of Patent: Oct. 18, 2011

(54) PHOSPHORESCENT HETERONUCLEAR COPPER(I)-IRIDIUM(III) COMPLEX AND ORGANIC ELECTROLUMINESCENCE DEVICE USING THE SAME

(75) Inventors: Das Rupasree Ragini, Yongin-si (KR); Hee-Kyung Kim, Yongin-si (KR); Byoung-Ki Choi, Yongin-si (KR); Yi-Yeol Lyu, Yongin-si (KR); Young-Hun Byun, Yongin-si (KR); O-Hyun Kwon, Yongin-si (KR); Che-Un Yang, Yongin-si (KR); Jung-Bae Song, Yongin-si (KR)

(73) Assignee: Samsung Mobile Display Co., Ltd., Giheung-Gu, Yongin, Gyunggi-Do (KR)

( * ) Notice: Subject to any disclaimer, the term of this patent is extended or adjusted under 35 U.S.C. 154(b) by 1237 days.

(21) Appl. No.: 11/727,593

(22) Filed: Mar. 27, 2007

(65) Prior Publication Data

US 2007/0267959 A1 Nov. 22, 2007

(30) Foreign Application Priority Data

May 19, 2006 (KR) .................. 10-2006-0045340

(51) Int. Cl.
*H01L 51/54* (2006.01)
*C09K 11/06* (2006.01)
(52) U.S. Cl. . 428/690; 428/917; 313/504; 257/E51.044; 548/101; 548/103; 548/106; 548/108; 546/2; 546/4; 546/10

(58) Field of Classification Search .................. None
See application file for complete search history.

(56) References Cited

FOREIGN PATENT DOCUMENTS

JP 2006-228936 8/2006

OTHER PUBLICATIONS

M. A. Baldo et al., "Excitonic singlet-triplet ratio in a semiconducting organic thin film", Physical Review B, vol. 60, No. 20, pp. 14 422-14 428, Nov. 1999.
M. A. Baldo et al., "Highly efficient phosphorescent emission from organic electroluminescent devices", Nature, vol. 395, Sep. 1998, pp. 151-154.
Mohammad A. Omary et al., "Blue Phosphors of Dinuclear and Mononuclear Copper(I) and Silver(I) Complexes of 3,5-Bis(trifluoromethyl)pyrazolate and the Related Bis(pyrazolyl)borate", Inorganic Chemistry, vol. 42, No. 26, pp. 8612-8614, 2003.
Machine translation of JP 2006-228936 (Aug. 2006), which was cited in the Office Action (Paper No. 20101117) mailed Nov. 24, 2010 of the related U.S. Appl. No. 11/802,066.

*Primary Examiner* — Marie R. Yamnitzky
(74) *Attorney, Agent, or Firm* — Robert E. Bushnell, Esq.

(57) ABSTRACT

Provided are a high-efficiency, photoluminescent heteronuclear copper (I)-iridium (III) complex and an organic electroluminescent device using the complex. The photoluminescent heteronuclear copper (I)-iridium (III) complex can be used to form an organic layer of an organic electroluminescent device, can emit light of 590-630 nm as a high-efficiency, photoluminescent material, and provides a high brightness and a low turn-on voltage.

21 Claims, 7 Drawing Sheets

PHOSPHORESCENT HETERONUCLEAR COPPER(I)-IRIDIUM(III) COMPLEX AND ORGANIC ELECTROLUMINESCENCE DEVICE USING THE SAME

CROSS-REFERENCE TO RELATED PATENT APPLICATION AND CLAIM OF PRIORITY

This application claims the benefit of Korean Patent Application No. 10-2006-0045340, filed on May 19, 2006, in the Korean Intellectual Property Office, the disclosure of which is incorporated herein in its entirety by reference.

BACKGROUND OF THE INVENTION

1. Field of the Invention

The present invention relates to a phosphorescent heteronuclear copper(I)-iridium(III) complex and an organic electroluminescence (EL) device using the same, and more particularly, to a luminescent heteronuclear copper(I)-iridium (III) complex emitting light in a red wavelength region (590-630 nm) and an organic electroluminescence device including the heteronuclear copper(I)-iridium(III) complex as an organic layer forming material.

2. Description of the Related Art

Organic electroluminescence (EL) devices are active display devices using the phenomenon of light generation occurring due to the recombination of electrons and holes in a fluorescent or phosphorescent organic compound thin layer (hereinafter, organic layer) when a current is applied to the organic layer. The Organic electroluminescence (EL) devices are lightweight, include simpler and less parts, have a structure that can be manufactured through simple processes, produce high-quality images, and have a wide viewing angle. Organic electroluminescent devices also can produce high-color purity moving pictures, and have low power consumption and a low driving voltage. Accordingly, organic electroluminescent devices have electrical characteristics suitable for portable electronic devices.

In general, an organic electroluminescent device has a structure including an anode, a hole transporting layer, an emitting layer, an electron transporting layer, and a cathode, which are sequentially stacked on a substrate. The hole transporting layer, the emitting layer, and the electron transporting layer are organic layers formed of organic compounds. The operating principle of the organic electroluminescent device having such a structure as described above is as follows. When a voltage is applied between the anode and the cathode, holes injected from the anode move to the emitting layer via the hole-transporting layer. Electrons are injected from the cathode to the emitting layer via the electron-transporting layer. Excitons are generated due to the recombination of carriers in the emitting. The excitons undergo radiative decay, emitting light having a wavelength corresponding to the band gap of a material.

Materials for forming the emitting layer of the organic electroluminescent device are classified into fluorescent materials using singlet-state excitons and phosphorescent materials using triplet-state excitons according to the emission mechanism. The emitting layer is formed by doping a fluorescent material or a phosphorescent material directly or doping a fluorescent material or a phosphorescent material on an appropriate host material. As a result of the electron excitation, singlet excitons and triplet excitons are generated in the host. Here, a statistical generation ratio between the singlet excitons and triplet excitons is 1:3 (Baldo, et al., Phys. Rev. B, 1999, 60, 14422).

In an organic electroluminescent device using a fluorescent material as a material for forming the emitting layer, triplet excitons that are generated in the host cannot be used. However, in an organic electroluminescent device using a phosphorescent material as a material for forming the emitting layer, both singlet excitons and triplet excitons can be used, and thus, a 100% internal quantum efficiency can be obtained (Baldo et al., Nature, Vol. 395, 151-154, 1998). Accordingly, the use of a phosphorescent materials leads to a higher light emitting efficiency than when a fluorescent material is used.

When a heavy metal, such as Ir, Pt, Rh, or Pd is included in an organic molecule, spin-orbital coupling occurs due to a heavy atom effect, and thus, singlet excitons and triplet excitons are mixed, thereby enabling transition to occur and thus effective phosphorescence even at room temperature can be obtained.

Various materials using transition metal compounds containing a transition metal, such as Iridium (Ir), platinum (Pt), etc. have been reported as high-efficient luminescent materials exhibiting phosphorescence. However, a phosphorescent material emitting light in a red wavelength region (590-630 nm) is still required for a high-efficiency, full-color display device.

Pyrazolate ligands are important in the coin metal chemistry. Pyrazolate ligands form a multinuclear complex by coordinating to a metal ion, such as Cu (I), Ag(I), Au(I), etc., in exo-bidentate mode. Coin metal pyrazolates can form a trimer, a tetramer, a hexamer, and up to a polymer according to the reaction conditions and the substituent in the pyrazolate moiety. Pyrazolate ligands improve the performance of an organic EL device by functioning as electron transporting moiety assisting the injection of electrons.

Among such coin metal pyrazolates, a multinuclear coin metal having a fluorinated pyrazolate ligand has very interesting light emitting characteristics. Fluorination facilitates thin film formation by assisting volatilization, improves thermal stability and stability of oxidation, and leads to a decrease in emission concentration quenching.

Mohammad et al (Mohammad A. Omary, Inorg. Chem., 2003, 42, 8612) disclose a copper pyrazolate complex with 2,4,6-collidine substituents. This complex emits bright blue light.

In addition, there is a continuous need for the fluorinated metal pyrazolate complex compounds that contain various ligands and the metal atoms that have excellent light emitting characteristics at non-blue wavelength regions.

SUMMARY OF THE INVENTION

The present invention provides a heteronuclear copper(I)-iridium(III) complex which can efficiently emit light in the red wavelength region of 590-630 nm.

The present invention also provides an organic electroluminescence (EL) device using the heteronuclear copper(I)-iridium(III) complex.

According to an aspect of the present invention, there is provided a heteronuclear copper(I)-iridium(III) complex represented by Formula 1.

[Formula 1]

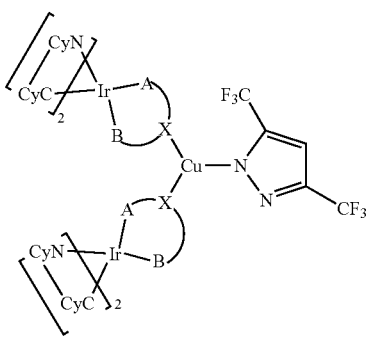

where A-X—B is a mononegative bidentate auxiliary ligand containing a hetero atom X;

X is N, P, S, or O;

CyN is a substituted or unsubstituted $C_3$-$C_{60}$ hetero ring group including nitrogen bound to iridium (III), or a substituted or unsubstituted $C_3$-$C_{60}$ heteroaryl group including nitrogen bound to iridium;

CyC is a substituted or unsubstituted $C_4$-$C_{60}$ cyclic group including carbon bound to iridium, a substituted or unsubstituted $C_3$-$C_{60}$ hetero ring group including carbon bound to iridium, a substituted or unsubstituted $C_3$-$C_{60}$ aryl group including carbon bound to iridium, or a substituted or unsubstituted $C_3$-$C_{60}$ heteroaryl group including carbon bound to iridium; and CyN-CyC indicates a cyclometalating ligand coordinated to iridium via the nitrogen of the CyN and the carbon of the CyC.

The present invention also provides a heteronuclear copper (I)-iridium(III) complex represented by Formula 2.

[Formula 2]

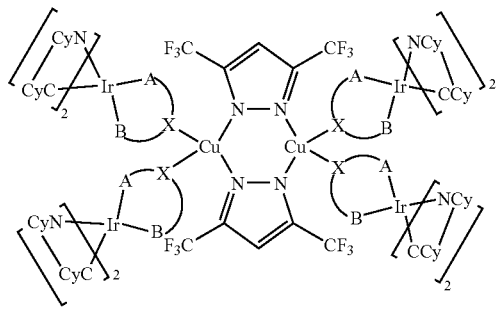

where X, A-X—B, CyC, CyN, and CyN-CyC are the same as defined above.

According to another aspect, the present invention provides a heteronuclear copper(I)-iridium(III) complex represented by Formula 3.

[Formula 3]

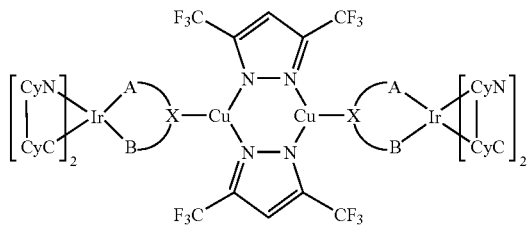

where X, A-X—B, CyN, CyC, and CyN-CyC are the same as defined above.

The compound of Formula 3 may be the compounds represented by Formula 4 or a compound represented by Formula 5.

[Formula 4]

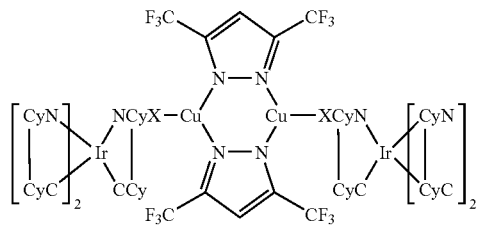

where X, CyN, and CyC are the same as defined as above;

CyC is a substituted or unsubstituted $C_4$-$C_{60}$ cyclic group including carbon bound to iridium, a substituted or unsubstituted $C_3$-$C_{60}$ hetero ring group including carbon bound to iridium, a substituted or unsubstituted $C_3$-$C_{60}$ aryl group including carbon bound to iridium, or a substituted or unsubstituted $C_3$-$C_{60}$ heteroaryl group including carbon bound to iridium;

NCyX is a substituted or unsubstituted $C_3$-$C_{60}$ hetero ring group including nitrogen that can be bound to iridium (III) and hetero atom X or a substituted or unsubstituted $C_3$-$C_{60}$ heteroaryl group including nitrogen bound to iridium and hetero atom X; and CyN-CyC and NCyX-CCy are cyclometalating ligands coordinated to iridium via the nitrogen of the CyN and the carbon of the CyC.

[Formula 5]

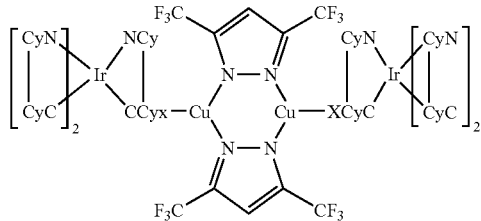

where X, CyN, and CyC are the same as defined above;

NCy is a substituted or unsubstituted $C_4$-$C_{60}$ cyclic group including nitrogen bound to iridium (III), a substituted or unsubstituted $C_3$-$C_{60}$ hetero ring group including nitrogen bound to iridium, a substituted or unsubstituted $C_3$-$C_{60}$ aryl group including nitrogen bound to iridium, or a substituted or unsubstituted $C_3$-$C_{60}$ heteroaryl group including nitrogen bound to iridium;

CCyX is a substituted or unsubstituted $C_3$-$C_{60}$ hetero ring group including carbon bound to iridium (III) and hetero atom X or a substituted or unsubstituted $C_3$-$C_{60}$ heteroaryl group including carbon bound to iridium and hetero atom X; and CyN-CyC and NCy-CCyX indicate cyclometalating ligands coordinated to iridium via the nitrogen of the CyN and the carbon of the CyC.

Examples of the ligands A-X—B in Formulae 1 through 3 are as follows:

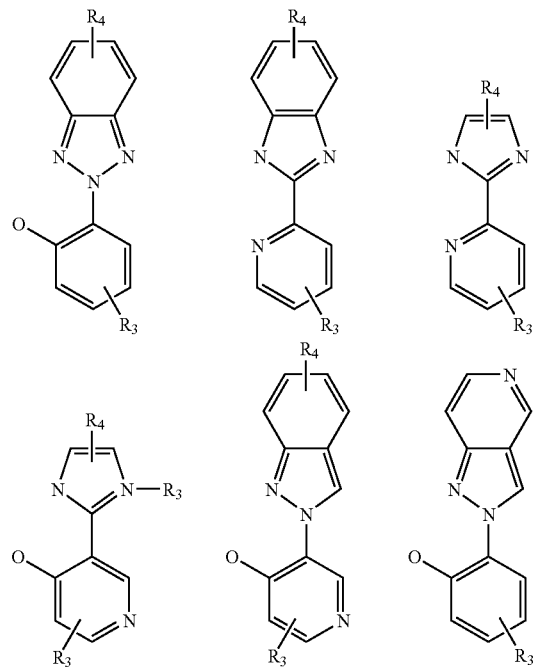

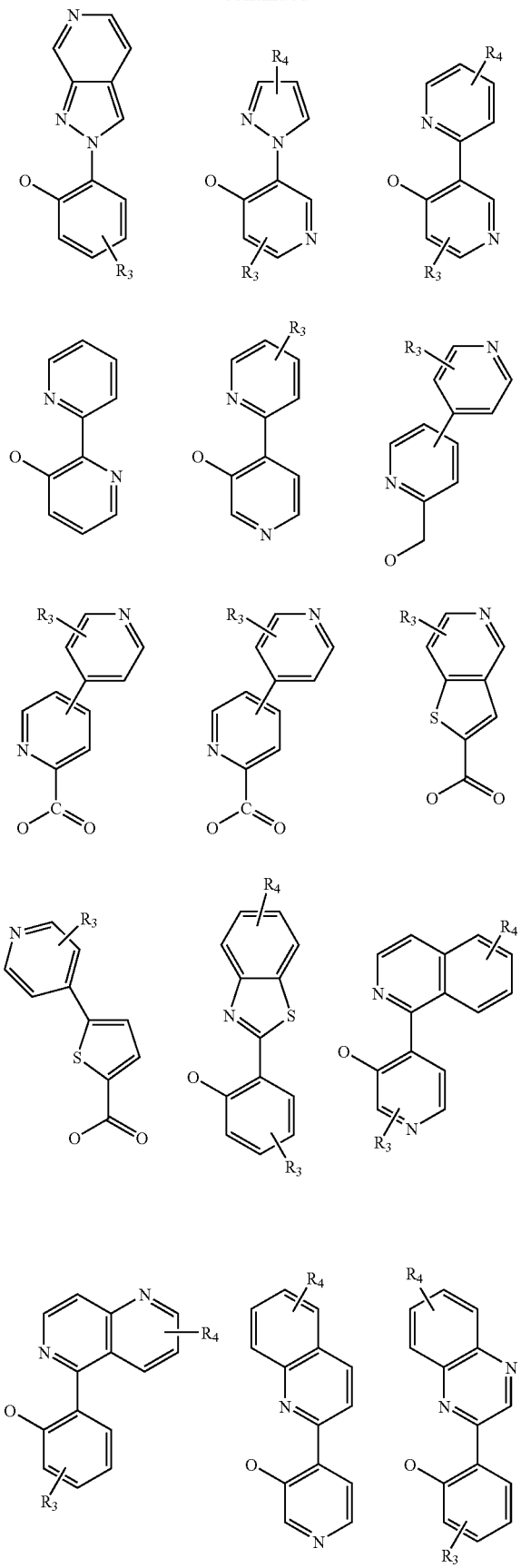
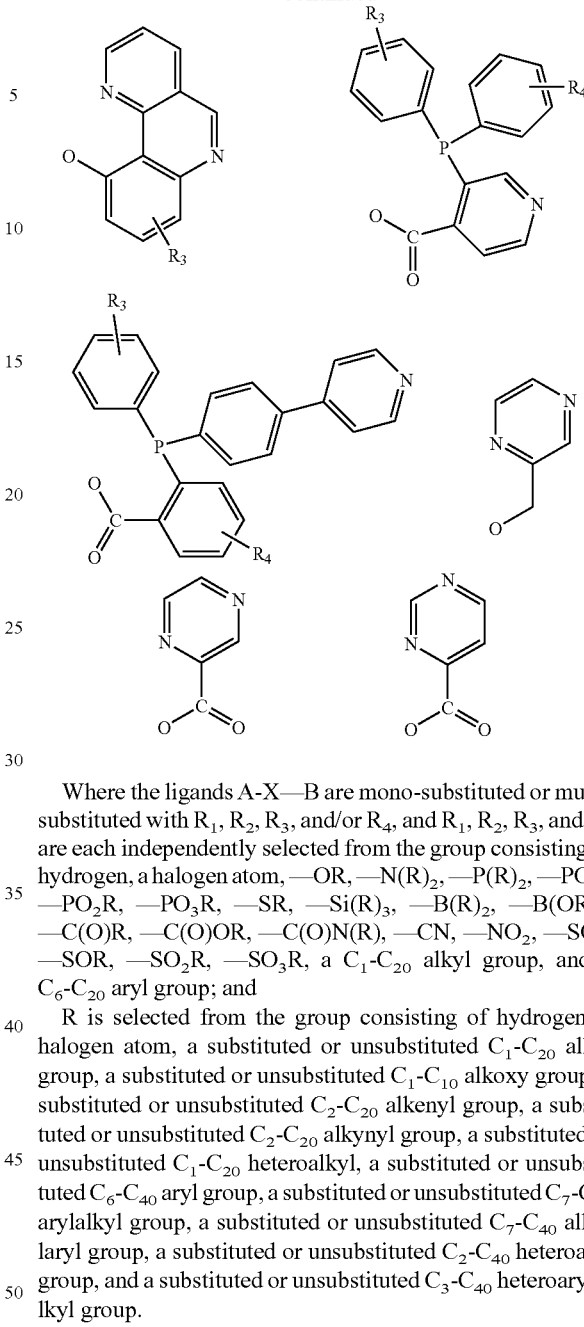

Where the ligands A-X—B are mono-substituted or multi-substituted with $R_1$, $R_2$, $R_3$, and/or $R_4$, and $R_1$, $R_2$, $R_3$, and $R_4$ are each independently selected from the group consisting of hydrogen, a halogen atom, —OR, —N(R)$_2$, —P(R)$_2$, —POR, —PO$_2$R, —PO$_3$R, —SR, —Si(R)$_3$, —B(R)$_2$, —B(OR)$_2$, —C(O)R, —C(O)OR, —C(O)N(R), —CN, —NO$_2$, —SO$_2$, —SOR, —SO$_2$R, —SO$_3$R, a $C_1$-$C_{20}$ alkyl group, and a $C_6$-$C_{20}$ aryl group; and R is selected from the group consisting of hydrogen, a halogen atom, a substituted or unsubstituted $C_1$-$C_{20}$ alkyl group, a substituted or unsubstituted $C_1$-$C_{10}$ alkoxy group, a substituted or unsubstituted $C_2$-$C_{20}$ alkenyl group, a substituted or unsubstituted $C_2$-$C_{20}$ alkynyl group, a substituted or unsubstituted $C_1$-$C_{20}$ heteroalkyl, a substituted or unsubstituted $C_6$-$C_{40}$ aryl group, a substituted or unsubstituted $C_7$-$C_{40}$ arylalkyl group, a substituted or unsubstituted $C_7$-$C_{40}$ alkylaryl group, a substituted or unsubstituted $C_2$-$C_{40}$ heteroaryl group, and a substituted or unsubstituted $C_3$-$C_{40}$ heteroarylalkyl group.

According to another aspect of the present invention, there is provided an organic EL device having an organic layer between a pair of electrodes, the organic layer containing the heteronuclear copper(I)-iridium(III) complex described above.

BRIEF DESCRIPTION OF THE DRAWINGS

A more complete appreciation of the present invention, and many of the above and other features and advantages of the present invention, will be readily apparent as the same becomes better understood by reference to the following detailed description when considered in conjunction with the accompanying drawings in which like reference symbols indicate the same or similar components, wherein.

DETAILED DESCRIPTION OF THE INVENTION

Figure 1A:
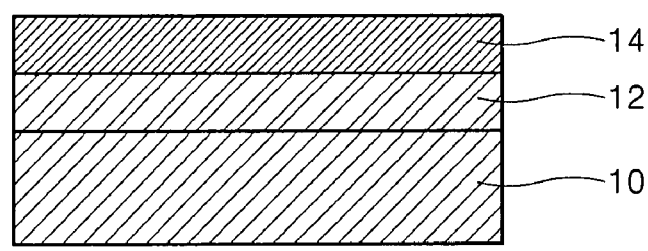
FIGS. 1A through 1F are diagrams schematically illustrating the laminated structures of organic electroluminescent (EL) devices according to an embodiment of the present invention.

Hereinafter, embodiments of the present invention will be described in detail.

The present invention provides heteronuclear copper (I)-iridium (III) complexes represented by Formula 1 through 3. The performance of the devices utilizing the copper (I)-iridium (III) complexes including a pyrazolate ligand, is improved due to the excellent electron transporting ability of pyrazole. In addition, due to a heteroaromatic ring coordinated to an iridium metal atom, red light can be effectively emitted.

[Formula 1]

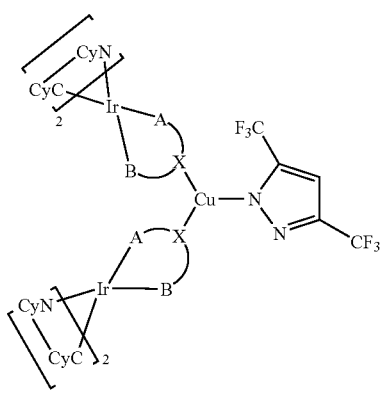

where A-X—B is a mononegative bidentate auxiliary ligand containing a hetero atom X;

X is N, P, S, or O;

CyN is a substituted or unsubstituted $C_3$-$C_{60}$ hetero ring group including nitrogen bound to iridium (III), or a substituted or unsubstituted $C_3$-$C_{60}$ heteroaryl group including nitrogen bound to iridium;

CyC is a substituted or unsubstituted $C_4$-$C_{60}$ cyclic group including carbon bound to iridium, a substituted or unsubstituted $C_3$-$C_{60}$ hetero ring group including carbon bound to iridium, a substituted or unsubstituted $C_6$-$C_{60}$ aryl group including carbon bound to iridium, or a substituted or unsubstituted $C_3$-$C_{60}$ heteroaryl group including carbon bound to iridium; and CyN-CyC indicates a cyclometalating ligand coordinated to iridium via nitrogen (N) and carbon (C).

[Formula 2]

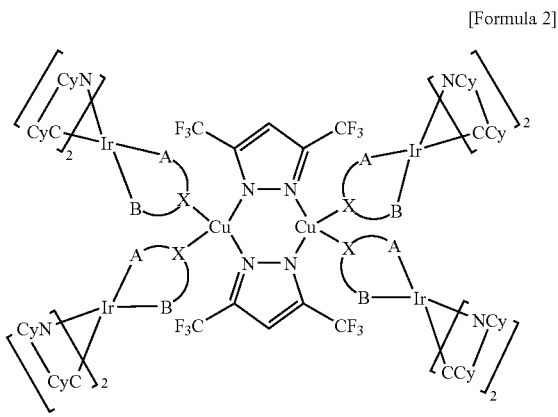

where X, A-X—B, CyN, CyC, CyN, and CyN-CyC are the same as defined above.

[Formula 3]

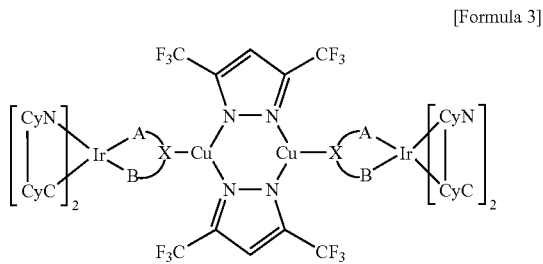

where X, A-X—B, CyC, CyN, and CyN-CyC are the same as defined above.

Examples of A-X—B in Formulas 1 through 3 are as follows:

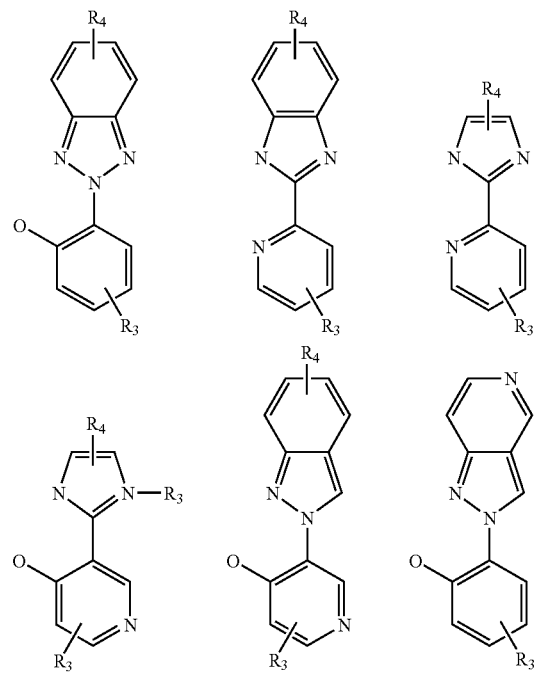

-continued

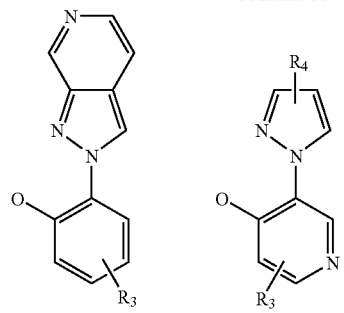
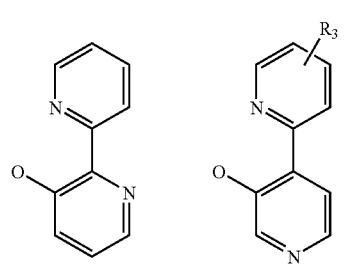
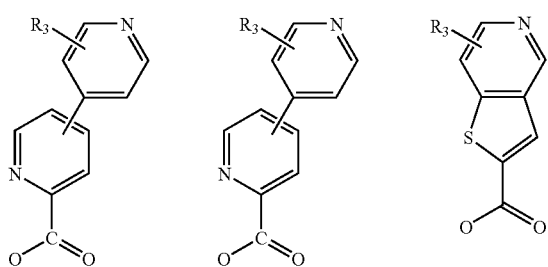
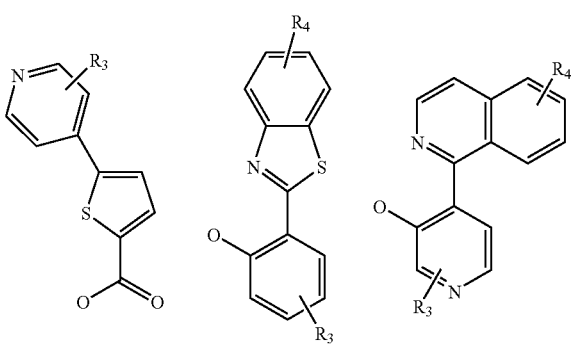
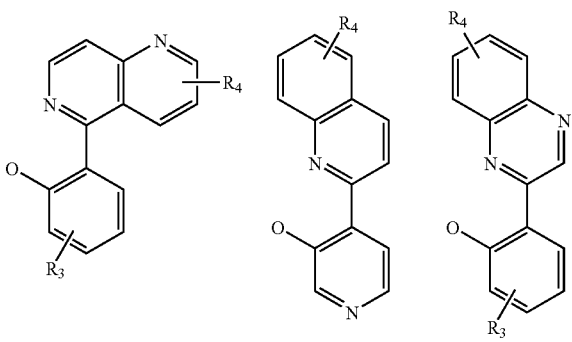

-continued

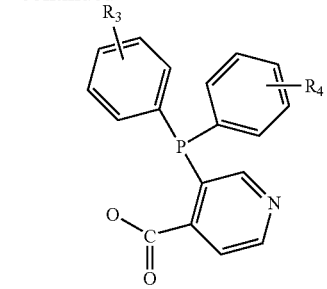
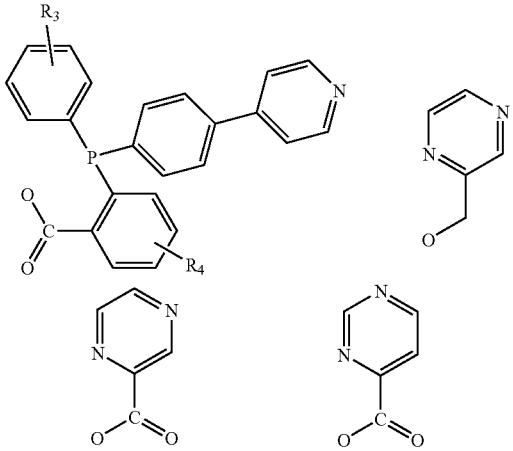

where the ligands A-X—B are mono-substituted or multi-substituted with $R_1$, $R_2$, $R_3$, and/or $R_4$, and $R_1$, $R_2$, $R_3$ and $R_4$ are each independently selected from the group consisting of hydrogen, a halogen atom, —OR, —N(R)$_2$, —P(R)$_2$, —POR, —PO$_2$R, —PO$_3$R, —SR, —Si(R)$_3$, —B(R)$_2$, —B(OR)$_2$, —C(O)R, —C(O)OR, —C(O)N(R), —CN, —NO$_2$, —SO$_2$, —SOR, —SO$_2$R, —SO$_3$R, a $C_1$-$C_{20}$ alkyl group, and a $C_6$-$C_{20}$ aryl group; and R is selected from the group consisting of hydrogen, a halogen atom, a substituted or unsubstituted $C_1$-$C_{20}$ alkyl group, a substituted or unsubstituted $C_1$-$C_{10}$ alkoxy group, a substituted or unsubstituted $C_2$-$C_{20}$ alkenyl group, a substituted or unsubstituted $C_2$-$C_{20}$ alkynyl group, a substituted or unsubstituted $C_1$-$C_{20}$ heteroalkyl, a substituted or unsubstituted $C_6$-$C_{40}$ aryl group, a substituted or unsubstituted $C_7$-$C_{40}$ arylalkyl group, a substituted or unsubstituted $C_7$-$C_{40}$ alkylaryl group, a substituted or unsubstituted $C_2$-$C_{40}$ heteroaryl group, and a substituted or unsubstituted $C_3$-$C_{40}$ heteroarylalkyl group.

In Formulae 1 through 3, CyN is a hetero ring group or heteroaryl group including nitrogen atom which directly forms a coordinate covalent bond to iridium, which is a core metal. The hetero ring group is a substituted or unsubstituted $C_3$-$C_{60}$ hetero ring group including a hetero atom such as N, O, S and/or P in the ring. Examples of the hetero ring group include pyrrolidine, morpholine, thiomorpholine, thiazolidine, and the like, but are not limited thereto. The heteroaryl group is a substituted or unsubstituted $C_3$-$C_{60}$ heteroaryl group including a hetero atom such as N, O, S, and/or P in the ring. Examples of the hetero ring group include pyridine, 4-methoxypyridine, quinoline, pyrrole, indole, pyrazine, pyrazole, imidazole, pyrimidine, quinazoline, thiazole, oxazole, triazine, 1,2,4-triazole, and the like, but are not limited thereto.

Regarding CyC in Formulae 1 through 3, examples of the substituted or unsubstituted $C_4$-$C_{60}$ cyclic group including carbon which is bound to iridium include cyclohexane, cyclopentane, and the like. Examples of the substituted or unsubstituted $C_3$-$C_{60}$ hetero ring group including carbon bound to iridium include tetrahydrofuran, 1,3-dioxane, 1,3-dithiane, 1,3-dithiolane, 1,4-dioxa-8-azaspiro[4,5]decane, 1,4-dioxaspiro[4,5]decan-2-one, and the like. Example of the substituted or unsubstituted $C_6$-$C_{60}$ aryl group including carbon bound to iridium include phenyl, 1,3-benzodioxole, biphenyl, naphthalene, anthracene, azulene, and the like. Example of the substituted or unsubstituted $C_3$-$C_{60}$ heteroaryl group including carbon bound to iridium include thiophene, furan2 (5H)-furanone, pyridine, coumarin, imidazole, 2-phenylpyridine, 2-benzothiazole, 2-benzooxazol, 1-phenylpyrazole, 1-naphthylpyrazole, 5-(4-methoxyphenyl)pyrazole, 2,5-bisphenyl-1,3,4-oxadilzole, 2,3-benzofuran, 2-(4-biphenyl)-6-phenyl benzooxazole, and the like.

In Formulae 1 through 3, each substituent of CyN-CyC may bind to each other to form a substituted or unsubstituted 4 to 7-membered ring group or a substituted or unsubstituted 4 to 7-membered hetero ring group, and in particular, a substituted or unsubstituted 4 to 7-membered fused ring or hetero ring group. Here, examples of the ring group or hetero ring group include a $C_3$-$C_{30}$ cycloalkyl group, a $C_3$-$C_{30}$ heterocycloalkyl group, a $C_6$-$C_{30}$ aryl group, and a $C_4$-$C_{30}$ heteroaryl group. The term "hetero" means the inclusion of a heteroatom, such as N, O, P, S, and a combination thereof, etc.

In the compounds of Formulae 1 through 3, at least one hydrogen can be substituted with various substituents. Examples of substituents include a halogen atom, —$OR_1$, —$N(R_1)_2$, —$P(R_1)_2$, —$POR_1$, —$PO_2R_1$, —$PO_3R_1$, —$SR_1$, —$Si(R_1)_3$, —$B(R_1)_2$, —$B(OR_1)_2$, —$C(O)R_1$, —$C(O)OR_1$, —$C(O)N(R_1)$, —CN, —$NO_2$, —$SO_2$, —$SOR_1$, —$SO_2R_1$, and —$SO_3R_1$. Here, $R_1$ is selected from the group consisting of hydrogen, a halogen atom, a substituted or unsubstituted $C_1$-$C_{20}$ alkyl group, a substituted or unsubstituted $C_1$-$C_{10}$ alkoxy group, a substituted or unsubstituted $C_2$-$C_{20}$ alkenyl group, a substituted or unsubstituted $C_2$-$C_{20}$ alkynyl group, a substituted or unsubstituted $C_1$-$C_{20}$ heteroalkyl group, a substituted or unsubstituted $C_6$-$C_{40}$ aryl group, a substituted or unsubstituted $C_7$-$C_{40}$ arylalkyl group, a substituted or unsubstituted $C_7$-$C_{40}$ alkylaryl group, a substituted or unsubstituted $C_2$-$C_{40}$ heteroaryl group, and a substituted or unsubstituted $C_3$-$C_{40}$ heteroarylalkyl group.

The compound of Formula 3 may be a compound represented by Formula 4 or a compound represented by Formula 5.

[Formula 4]

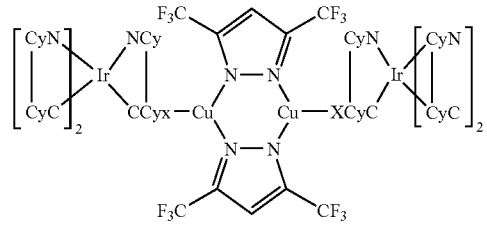

where X, CyN, and CyC are the same as defined above;

CCy is a substituted or unsubstituted $C_4$-$C_{60}$ cyclic group including carbon bound to iridium, a substituted or unsubstituted $C_3$-$C_{60}$ hetero ring group including carbon bound to iridium, a substituted or unsubstituted $C_6$-$C_{60}$ aryl group including carbon bound to iridium, or a substituted or unsubstituted $C_3$-$C_{60}$ heteroaryl group including carbon bound to iridium;

NCyX is a substituted or unsubstituted $C_3$-$C_{60}$ hetero ring group including nitrogen bound to iridium (III) and hetero atom X or a substituted or unsubstituted $C_3$-$C_{60}$ heteroaryl group including nitrogen bound to iridium and hetero atom X; and CyN-CyC and NCyX-CCy are cyclometalating ligands coordinated to iridium via nitrogen and carbon.

[Formula 5]

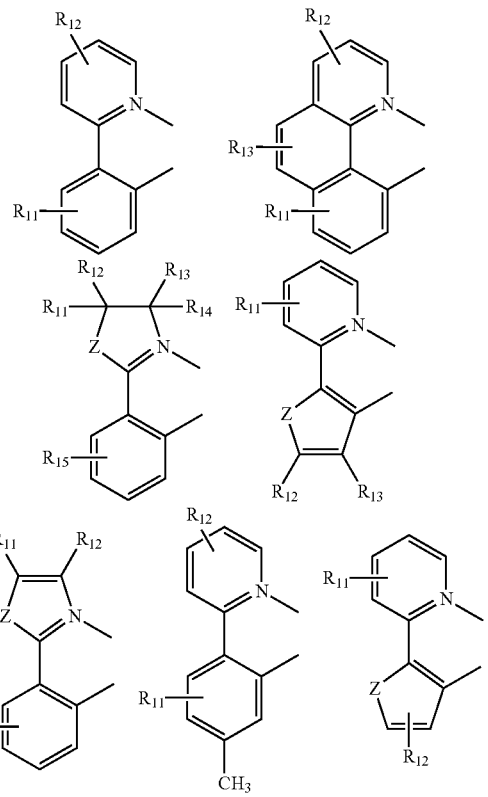

where X, CyN, and CyC are the same as defined above;

NCy is a substituted or unsubstituted $C_4$-$C_{60}$ cyclic group including nitrogen bound to iridium (III), a substituted or unsubstituted $C_3$-$C_{60}$ hetero ring group including nitrogen bound to iridium, a substituted or unsubstituted $C_3$-$C_{60}$ aryl group including nitrogen bound to iridium, or a substituted or unsubstituted $C_3$-$C_{60}$ heteroaryl group including nitrogen bound to iridium;

CCyX is a substituted or unsubstituted $C_3$-$C_{60}$ hetero ring group including carbon bound to iridium (III) and hetero atom X or a substituted or unsubstituted $C_3$-$C_{60}$ heteroaryl group including carbon bound to iridium and hetero atom X; and CyN-CyC and NCy-CCyX indicate cyclometalating ligands coordinated to iridium via nitrogen and carbon.

Examples of the cyclometalating ligand (CyN-CyC) in Formulae 1 through 5 are as follows, but are not limited thereto.

-continued
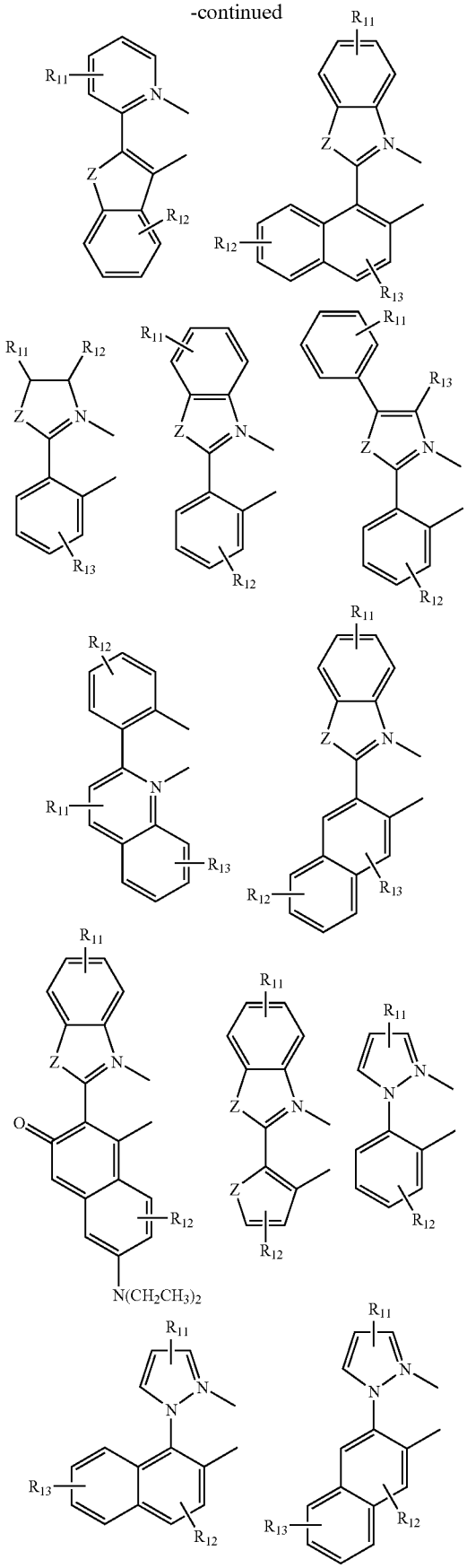
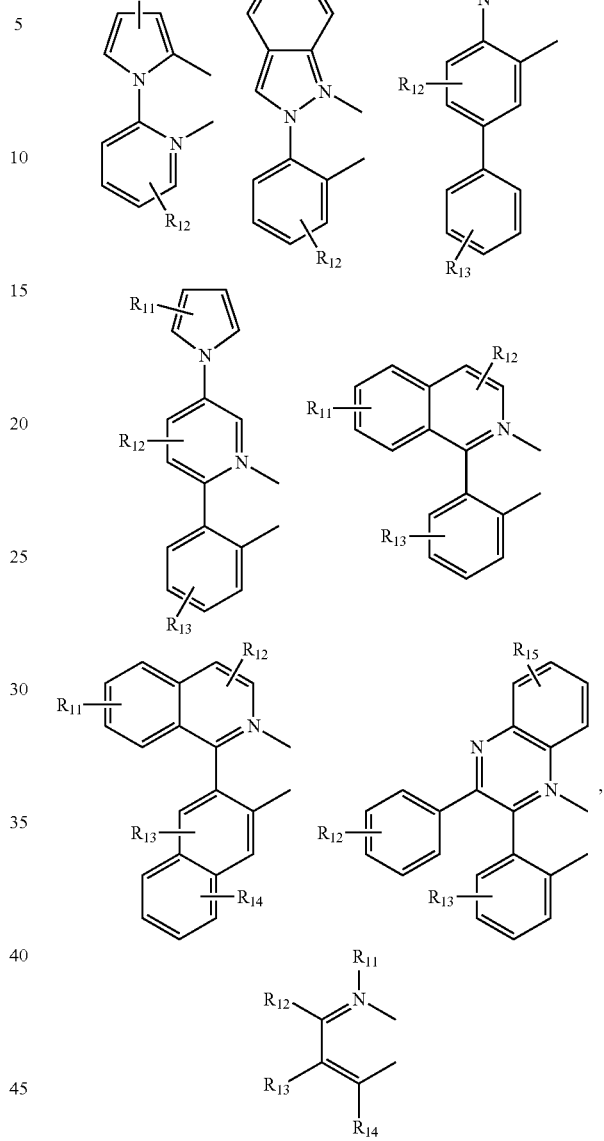
alternatively to the above definition of CyN and CyC, CyN-CyC may be
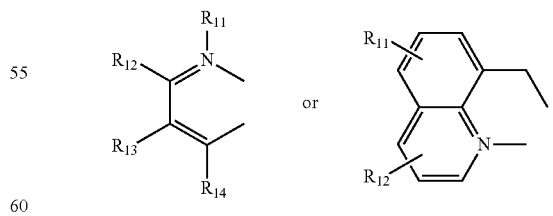
where the cyclometalating ligand (CyN-CyC) are mono-substituted or multi-substituted with $R_{11}$, $R_{12}$, $R_{13}$, $R_{14}$, and/or $R_{15}$, and $R_{11}$, $R_{12}$, $R_{13}$, $R_{14}$, and $R_{15}$ are each independently selected from the group consisting of hydrogen, a halogen atom, —OR, —N(R)$_2$, —P(R)$_2$, —POR, —PO$_2$R, —PO$_3$R, —SR, —Si(R)$_3$, —B(R)$_2$, —B(OR)$_2$, —C(O)R, —C(O)OR, —C(O)N(R), —CN, —NO$_2$, —SO$_2$, —SOR, —SO$_2$R, —SO$_3$R, a C$_1$-C$_{20}$ alkyl group, and a C$_6$-C$_{20}$ aryl group;

R is selected from the group consisting of hydrogen, a halogen atom, a substituted or unsubstituted C$_1$-C$_{20}$ alkyl group, a substituted or unsubstituted C$_1$-C$_{10}$ alkoxy group, a substituted or unsubstituted C$_2$-C$_{20}$ alkenyl group, a substituted or unsubstituted C$_2$-C$_{20}$alkynyl group, a substituted or unsubstituted C$_1$-C$_{20}$ heteroalkyl, a substituted or unsubstituted C$_6$-C$_{40}$ aryl group, a substituted or unsubstituted C$_7$-C$_{40}$ arylalkyl group, a substituted or unsubstituted C$_7$-C$_{40}$ alkylaryl group, a substituted or unsubstituted C$_2$-C$_{40}$ heteroaryl group, and a substituted or unsubstituted C$_3$-C$_{40}$ heteroarylalkyl group; and Z is S, O, or NR$_0$ where R$_0$ is hydrogen or a C$_1$-C$_{20}$alkyl group.

In Formulae 1 through 3, examples of A and B include: a C$_2$-C$_8$ cycloalkyl group, such as cyclohexyl, cyclopentyl, cyclooctyl, etc.; a C$_6$-C$_{20}$ aryl group, such as phenyl, 1,3-benzodioxole, biphenyl, naphthalene, anthracene, azulene, etc.; a C$_1$-C$_{20}$ heteroaryl group, such as thiophene, furan2 (5H)-furanone, pyridine, coumarin, imidazole, 2-phenylpyridine, 2-benzothiazole, 2-benzooxazole, 1-phenylpyrazole, 1-naphthylpyrazole, 5-(4-methoxyphenyl)pyrazole, 2,5-bisphenyl-1,3,4-oxadiazole, 2,3-benzofurane2-(4-biphenyl)-6-phenyl benzooxazole, etc.

Examples of a silyl group includes triarylsilyl, trialkylsilyl, etc. Examples of a boryl group include dialkylboryl, diarylboryl, difluoroboryl, difluoroheteroarylboryl, etc.

Examples of electron transporting moieties A-X—B include quinolyl, substituted quinolyl, imidazolyl, substituted imidazolyl, benzimidazolyl, substituted benzimidazolyl, triazolyl, substituted triazolyl, oxazolyl, substituted oxazolyl, 1,10-phenanthrolyl, substituted 1,10-phenanthrolyl, quinoxalinyl, substituted quinoxalinyl, etc.

Examples of NCyX-CCy in Formula 4 are as follows.

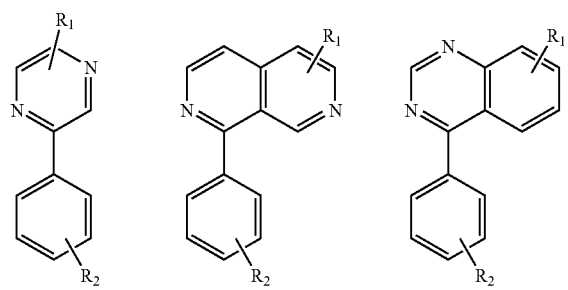

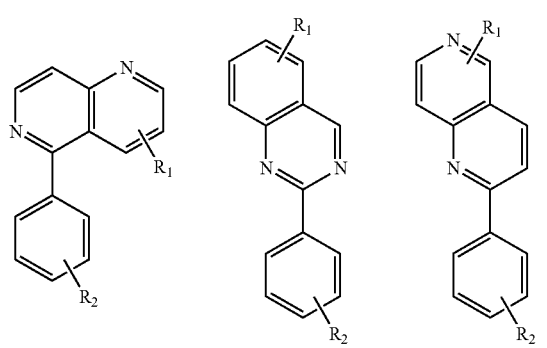

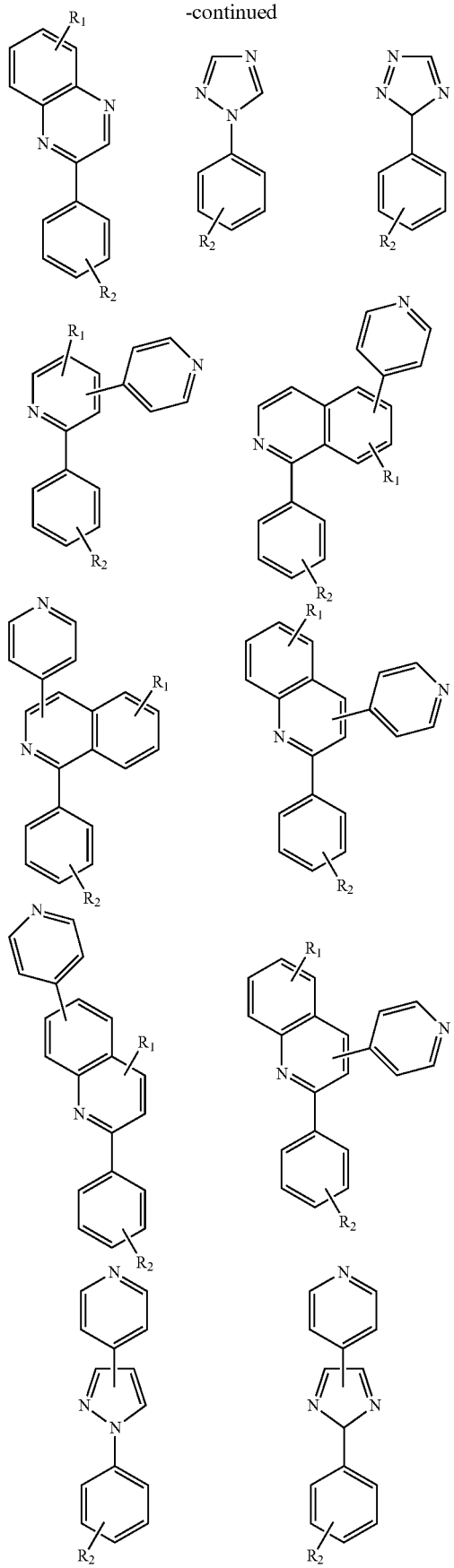

Examples of NCy-CCyX in Formula (5) are as follows:

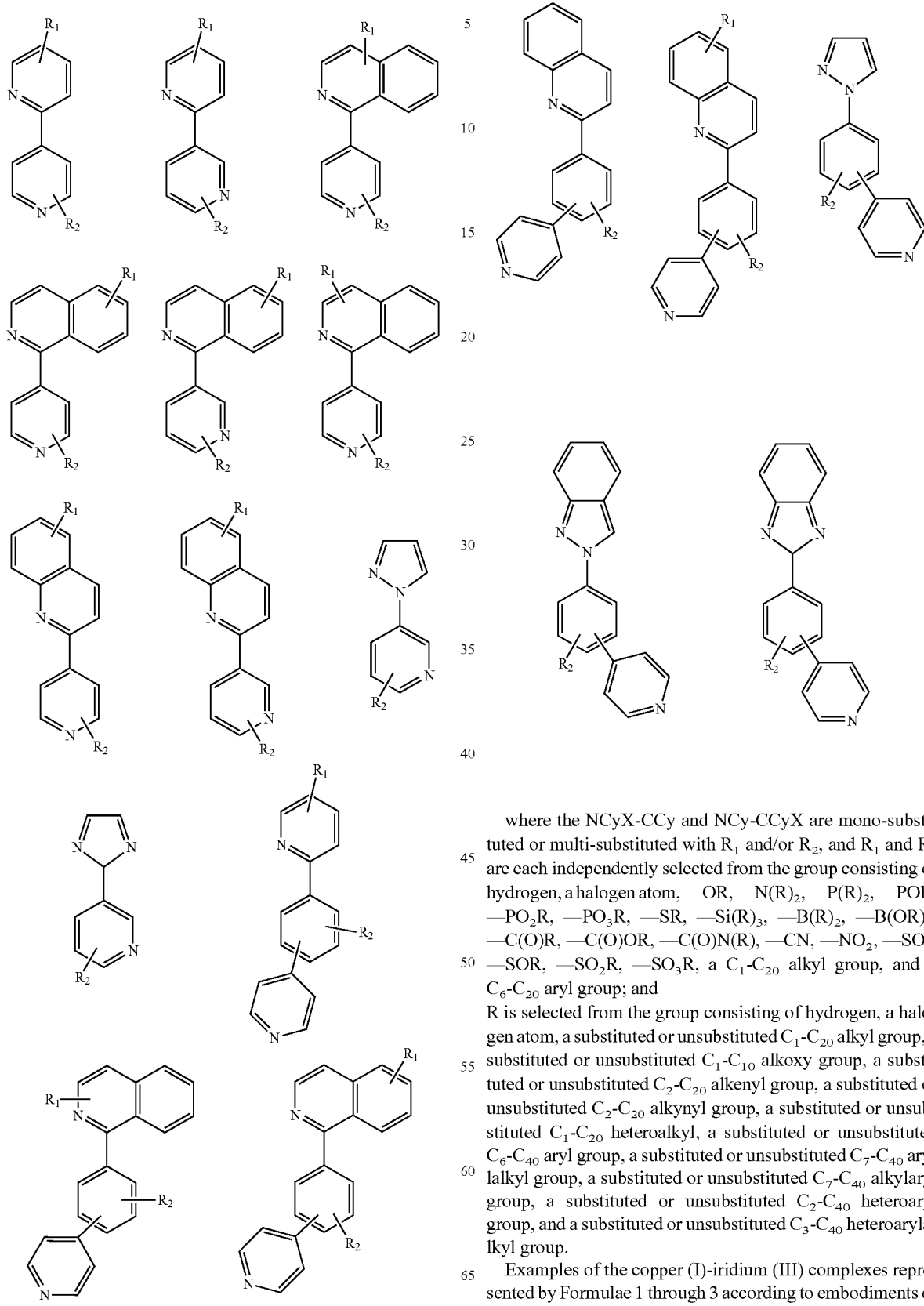

where the NCyX-CCy and NCy-CCyX are mono-substituted or multi-substituted with $R_1$ and/or $R_2$, and $R_1$ and $R_2$ are each independently selected from the group consisting of hydrogen, a halogen atom, —OR, —N(R)$_2$, —P(R)$_2$, —POR, —PO$_2$R, —PO$_3$R, —SR, —Si(R)$_3$, —B(R)$_2$, —B(OR)$_2$, —C(O)R, —C(O)OR, —C(O)N(R), —CN, —NO$_2$, —SO$_2$, —SOR, —SO$_2$R, —SO$_3$R, a $C_1$-$C_{20}$ alkyl group, and a $C_6$-$C_{20}$ aryl group; and R is selected from the group consisting of hydrogen, a halogen atom, a substituted or unsubstituted $C_1$-$C_{20}$ alkyl group, a substituted or unsubstituted $C_1$-$C_{10}$ alkoxy group, a substituted or unsubstituted $C_2$-$C_{20}$ alkenyl group, a substituted or unsubstituted $C_2$-$C_{20}$ alkynyl group, a substituted or unsubstituted $C_1$-$C_{20}$ heteroalkyl, a substituted or unsubstituted $C_6$-$C_{40}$ aryl group, a substituted or unsubstituted $C_7$-$C_{40}$ arylalkyl group, a substituted or unsubstituted $C_7$-$C_{40}$ alkylaryl group, a substituted or unsubstituted $C_2$-$C_{40}$ heteroaryl group, and a substituted or unsubstituted $C_3$-$C_{40}$ heteroarylalkyl group.

Examples of the copper (I)-iridium (III) complexes represented by Formulae 1 through 3 according to embodiments of the present invention include the following compounds.

[Formula 6]
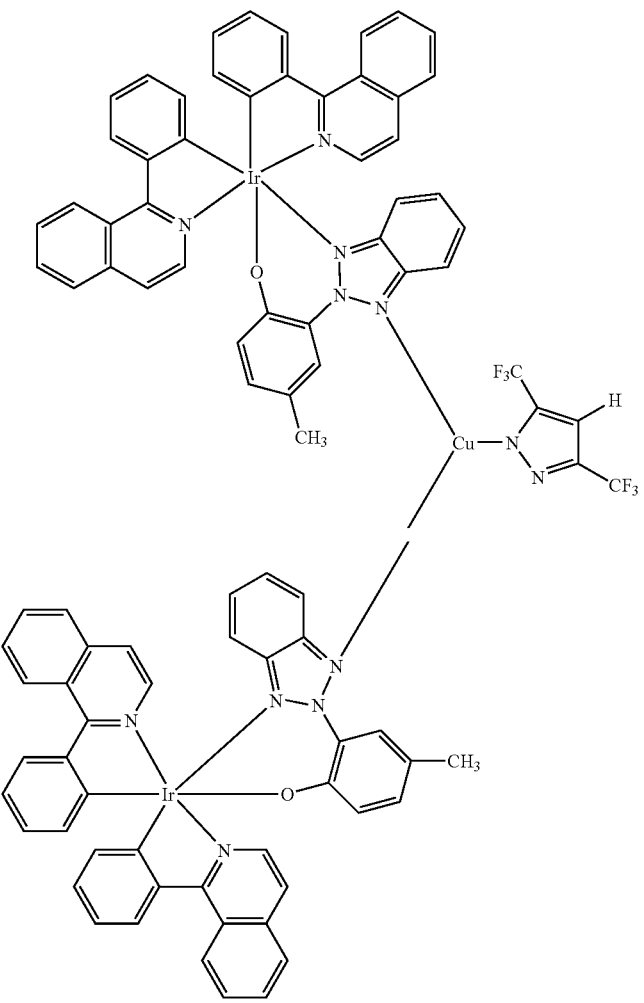
[Formula 7]
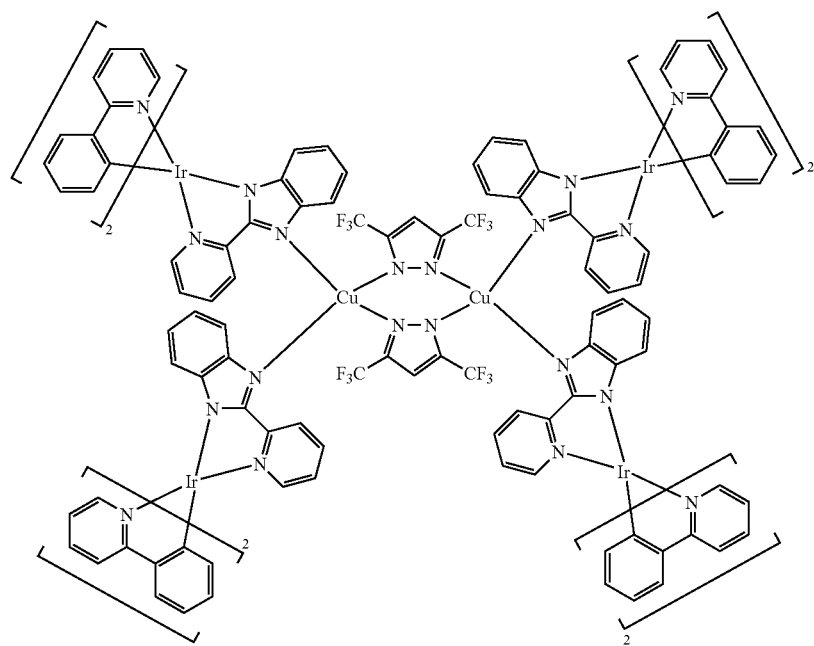

[Formula 8]
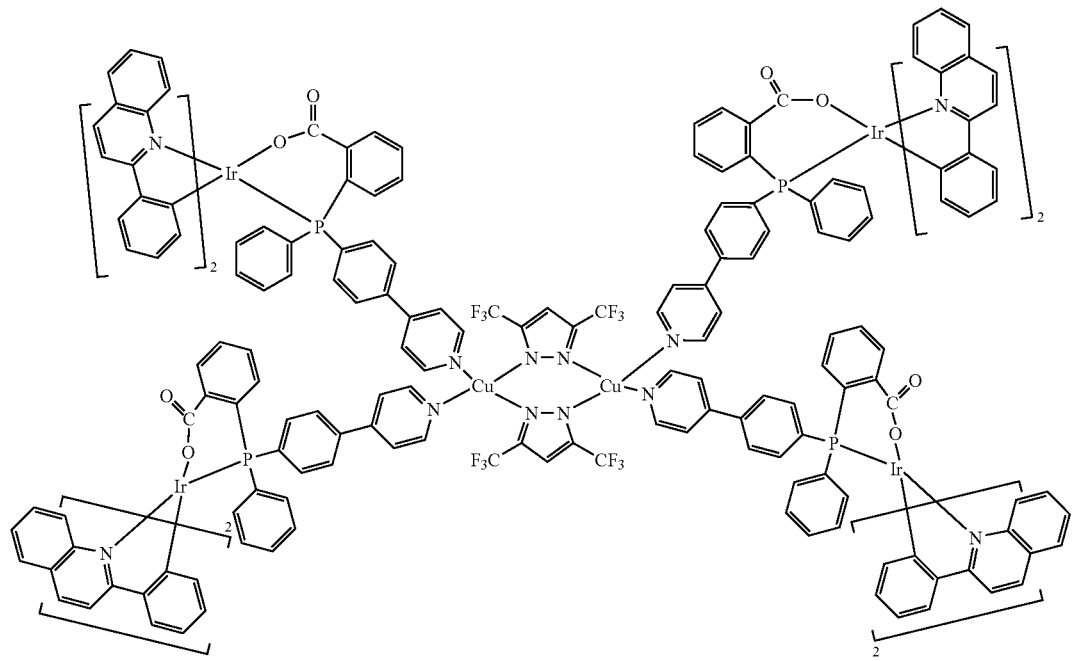
[Formula 9]
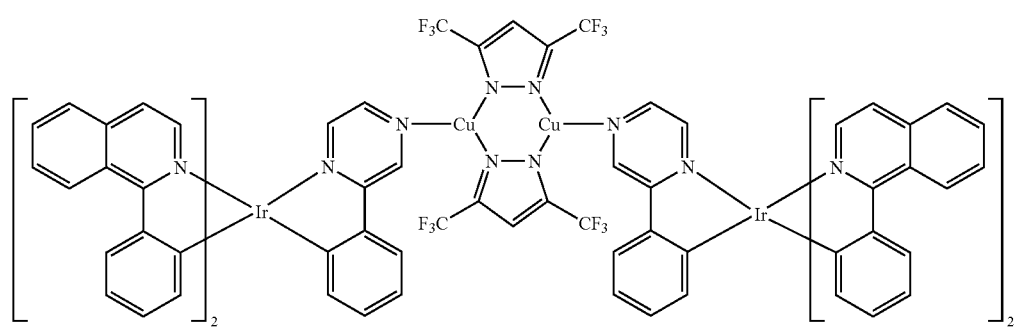
[Formula 10]
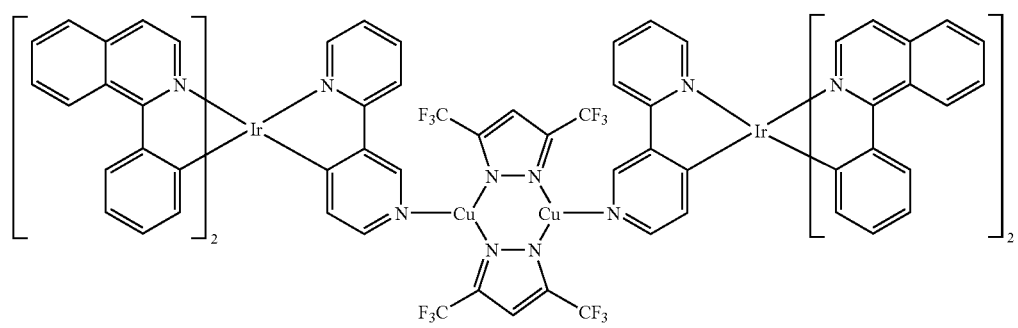

The copper (I)-iridium (III) complexes represented by Formulae 1 through 3 according to embodiments of the present invention can be synthesized by reacting a compound of Formula 11 [(3,5-(CF$_3$)$_2$Pz)-Cu]$_3$ below with a compound of Formula 12.

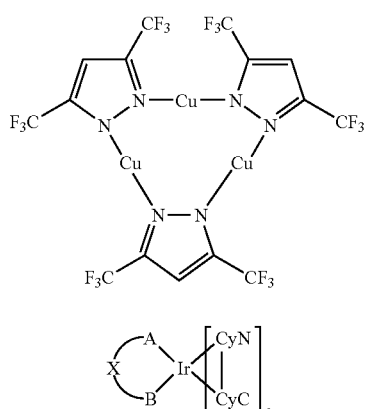

[Formula 11]

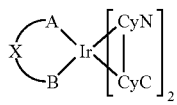

[Formula 12]

In Formula 12 above, A-X—B, X, CyN, CyC, and CyN-CyC are the same as defined in connection with Formula 1 above.

A method of preparing a representative compound of Formula 1 is illustrated in Reaction Scheme 1 below by showing a method of synthesizing an exemplary copper (I)-iridium (III) complex represented by Formula 6.

<Reaction Scheme 1>

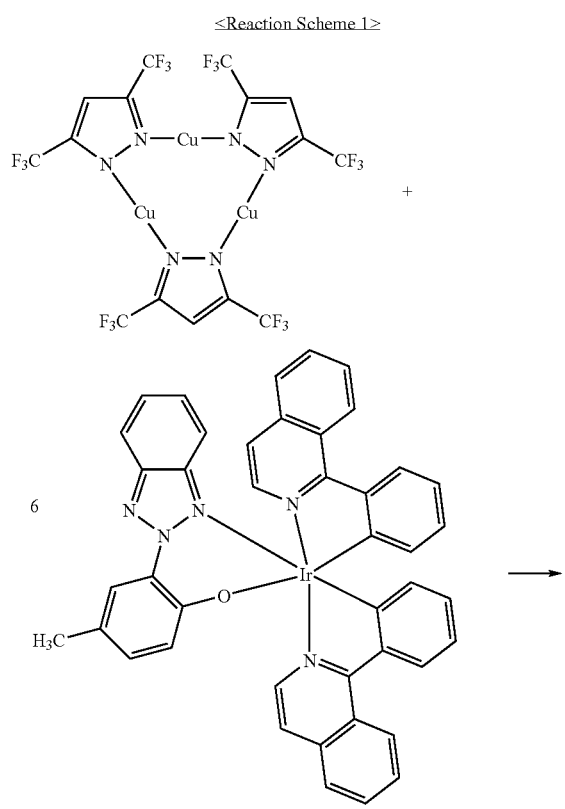

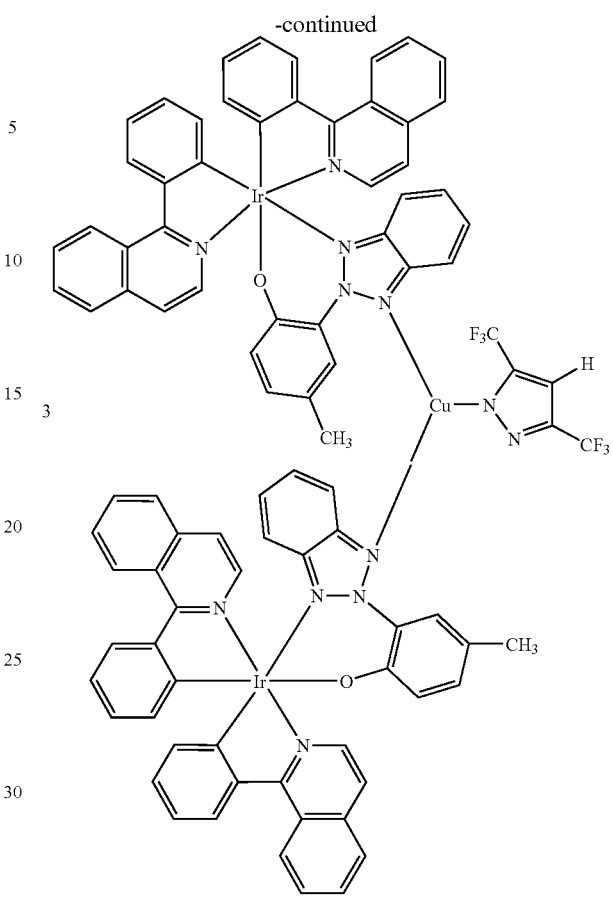

The reaction in Reaction Scheme 1 may be performed in a solvent, such as benzene, in a mole ratio of 1:6 between the compound of Formula 11 and the compound of Formula 12 for 12 to 16 hours.

An organic EL device according to an embodiment of the present invention includes an organic layer, and for example, an emitting layer, formed of one of the copper (I)-iridium (III) complexes of Formulae 1 through 3. Here, the copper (I)-iridium (III) complexes of Formulae 1 through 3 are very useful phosphorescent dopants used to form the emitting layer and exhibit excellent light emitting characteristics in a red wavelength region (590-630 nm).

When a copper (I)-iridium (III) complex represented by one of Formulae 1 through 3 is used as phosphorescent dopant, the organic layer may further include at least one host selected from the group consisting of at least one kind of a polymer host, a mixed host of a polymer and a low-molecular weight material, a low-molecular weight host, and a non-emitting polymer matrix. Here, any polymer host, low-molecular weight host, and non-emitting polymer matrix, which are commonly used to form the emitting layer of an organic EL device can be used. Examples of the polymer host include poly(vinylcarbazole) (PVK), polyfluorene, etc., but are not limited thereto. Examples of the low-molecular weight host include CBP(4,4'-N,N'-dicarbazole-biphenyl), 4,4'-bis[9-(3,6-biphenylcarbazolyl)]-1,1'-biphenyl, 9,10-bis[(2',7'-t-butyl)-9',9''-spirobifluorenyl anthracene, terafluorene, etc., but are not limited thereto. Examples of the non-emitting polymer matrix include, polymethylmethacrylate, polystyrene, etc., but are not limited thereto.

The amount of the copper (I)-iridium (III) complex represented by one of Formulae 1 through 3 may be, for example, in a range of 1 to 30 parts by weight based on 100 parts by weight of the emitting layer forming material. When the amount of the copper (I)-iridium (III) complex is less than 1 part by weight, the amount of the luminescent material is insufficient, and thus, the efficiency and lifetime decrease. When the amount of the copper (I)-iridium (III) complex is above 30 parts by weight, triplet excitons quench, and thus, the efficiency decreases.

In addition, when incorporating the copper (I)-Iridium (III) complex into the emitting layer, various methods, such as vacuum deposition, sputtering, printing, coating, ink-jetting, etc. can be used.

Moreover, when the copper (I)-iridium (III) complexes represented by Formulae 1 through 3 can emit white light when used together with a green luminescent material or a blue luminescent material.

FIGS. 1A through 1F are diagrams schematically illustrating laminated structures of organic EL devices according to embodiments of an embodiment of the present invention.

Referring to FIG. 1A, an emitting layer 12 containing the copper (I)-iridium (III) complex of one of Formulae 1 through 3 is formed on a first electrode 10, and a second electrode 14 is formed on the emitting layer 12.

Figure 1B:
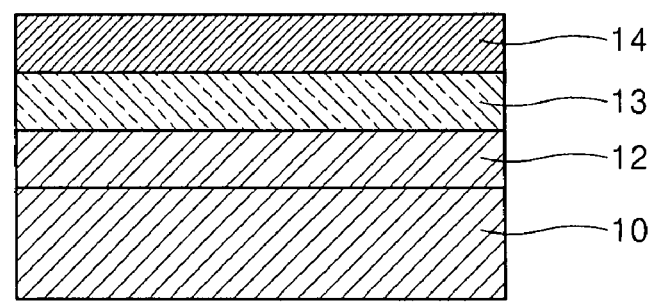

Referring to FIG. 1B, the emitting layer 12 containing the copper (I)-iridium (III) complex of one of Formulae 1 through 3 is formed on the first electrode 10, a hole blocking layer (HBL) 13 is formed on the emitting layer 12, and the second electrode 14 is formed on the HBL 13.

Figure 1C:
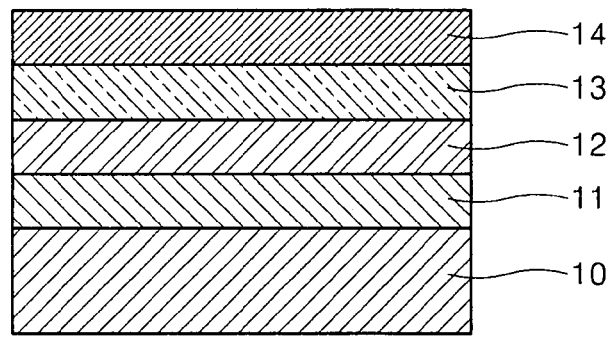

An organic EL device in FIG. 1C further includes a hole injection layer (HIL) 11 formed between the first electrode 10 and the emitting layer 12.

Figure 1D:
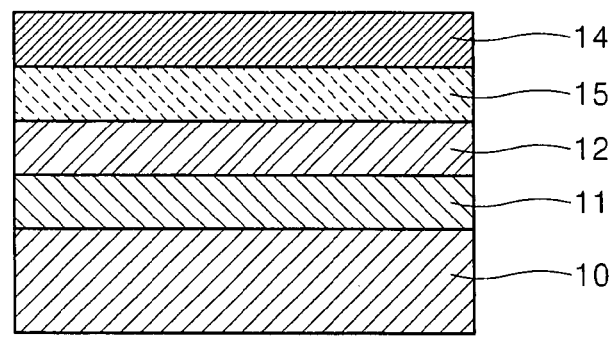

An organic EL device in FIG. 1D has the same laminated structure as the organic EL device in FIG. 1C, except that an electron transporting layer (ETL) 15 instead of the HBL 13 is formed on the emitting layer 12.

Figure 1E:
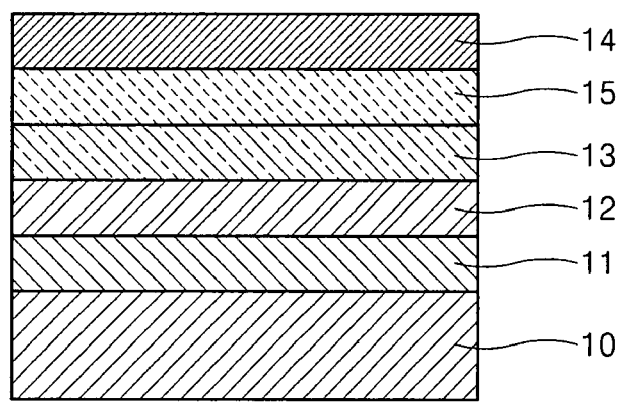

An organic EL device in FIG. 1E has the same laminated structure as the organic EL device in FIG. 1C, except that two layers, i.e., the HBL 13 and the ETL 15, instead of the single HBL 13, are sequentially formed on the emitting layer 12 containing the copper (I)-Iridium (III) complex of one of the compounds of Formulae 1 through 3. The organic EL device of FIG. 1E may further include an electron injecting layer between the ETL 15 and the second electrode 14 if required.

Figure 1F:
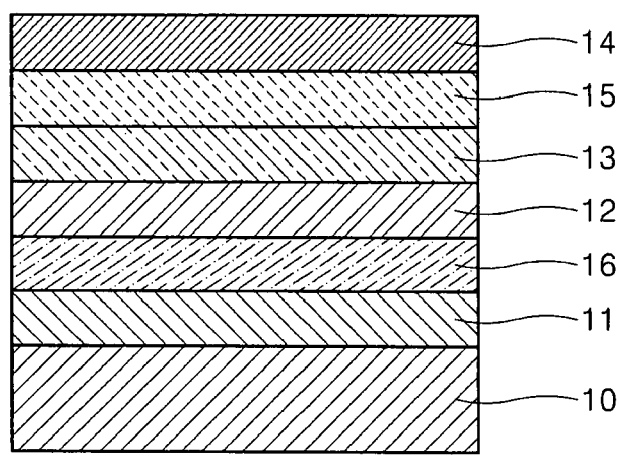

An organic EL device of FIG. 1F has the same structure as the organic EL device of FIG. 1E, except that a hole transporting layer (HTL) 16 is further formed between the HIL 11 and the emitting layer 12. The HTL 16 prevents the impurities from the HIL 11 into the emitting layer 12.

An organic EL device having such a laminated structure as described above may be manufactured using a general method without limitations. The organic layer may have a thickness of 30-100 nm. When the thickness of the organic layer is smaller than 30 nm, the efficiency and lifetime thereof decrease. When the thickness of the organic layer is greater than is 100 nm, the operating voltage increases.

The organic layer means a layer formed of an organic compound between a pair of electrodes in an organic EL device. For example, the organic layer may be the emitting layer, the electron transporting layer, the hole transporting layer, etc.

In the organic EL device, a buffer layer may be each interposed between the layers. A material for the buffer layer can be any material commonly used in the field. Examples of a material for the buffer layer commonly include copper phthalocyanine, polythiophene, polyaniline, polyacetylene, polypyrrole, polyphenylene vinylene, and a derivative thereof, but are not limited thereto.

A material for the hole transporting layer (HTL) can be any material commonly used in the field, for example, polytriphenylamine, but is not limited thereto.

A material for the electron transporting layer (ETL) can be any material commonly used in the field, for example, polyoxadiazole, but is not limited thereto.

A material for the hole blocking layer (HBL) can be any material commonly used in the field, for example, LiF, $BaF_2$, or $MgF_2$, but is not limited thereto.

An organic EL device according to the embodiments of the present invention can be manufactured without using a special equipment and method. For example, an organic EL device according to an embodiment of the present invention can be manufactured according to a method of manufacturing an organic EL device using a common luminescent material.

The copper (I)-iridium (III) complexes of Formulae 1 through 3 according to embodiments of the present invention can emit light having a wavelength of about 590-630 nm. A light emitting diode using the copper (I)-iridium (III) complexes can be used in a light source for full-color display, a backlight, an outdoor board, optical communication, interior decoration, etc.

Hereinafter, embodiments of the present invention will be described in greater detail with reference to the following examples. The following examples are for illustrative purposes only and are not intended to limit the scope of the invention.

REFERENCE EXAMPLE 1

Synthesis of $[(3,5-(CF_3)_2Pz)Cu]_3$

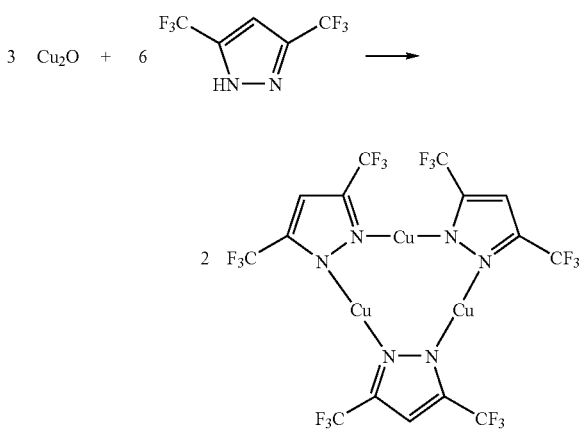

0.40 g (1.90 mmole) of $Cu_2O$ and 1 g (4.9 mmole) of 3,5-trifluoromethyl pyrazole were added to 20-30 mL of benzene and reacted at 60° C. for 48-72 hours. The reaction product was cooled at a reduced pressure, and the solvent was evaporated from the reaction mixture. Resulting white powder was recrystallized using a mixture of benzene and hexane.

$^1$H NMR $CDCl_3$: ppm 6.97 (s, 1H, CH), 13.07-11.23 (broad, NH)

EXAMPLE 1

Synthesis of Compound of Formula 6

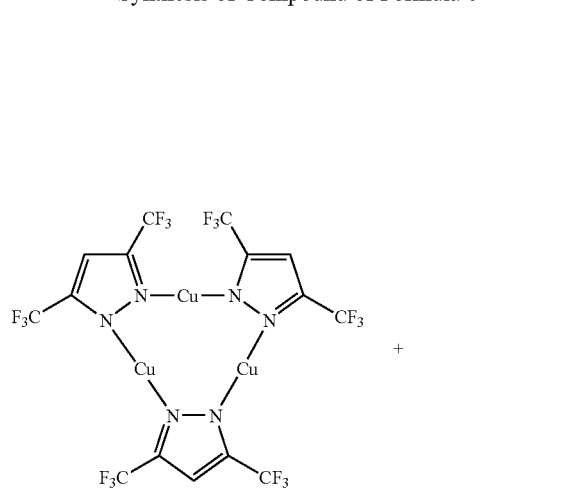

+

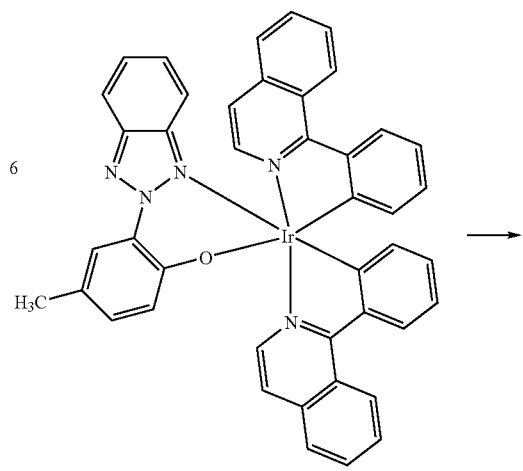

→

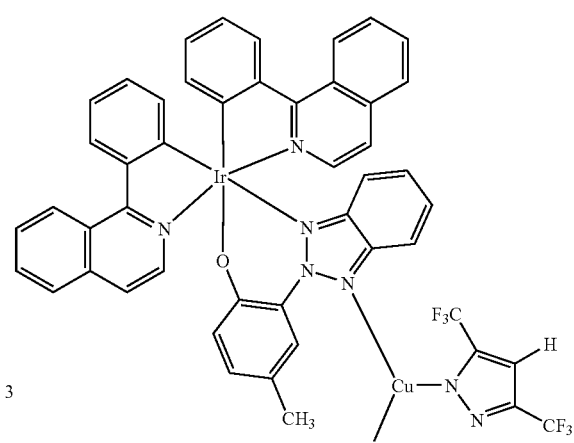

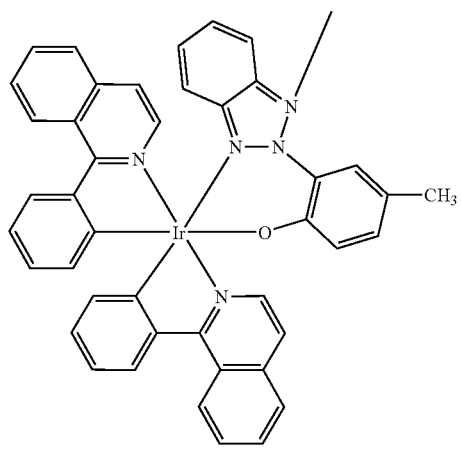

0.50 g (0.6 mmole) of IrPIQOBT (bis-[N,C'-2-phenylisoquinoliato]1-(2-hydroxyphenyl)benzo-1,2,5-triazolato Iridium (III)) and 0.080 g (0.1 mmole) of [(3,5-trifluoromethylpyrazolato)Cu]$_3$ [(3,5-(CF$_3$)$_2$Pz)-Cu]$_3$ were added to 20-30 mL of benzene and reacted at room temperature for 12-16 hours. The reaction product was filtered at a reduced pressure, and the solvent was evaporated from the reaction product. A resulting red solid product was recrystallized using a mixture of benzene and hexane.

$^1$H NMR CDCl$_3$: ppm 9.15-9.04 (m, 2H), 8.91 (d, 1H), 8.42 (d, 1H), 8.14 (d, 1H), 7.95 (d, 1H), 7.88 (t, 2H), 7.82-7.74 (m, 3H), 7.70-7.65 (dd, 2H), 7.63 (d, 1H), 7.37 (s, 0.5H), 7.34 (d, 1H), 7.17 (t, 1H), 7.12-7.00 (m, 2H), 6.94 (t, 1H), 6.94-6.66 (m, 4H), 6.49 (d, 1H), 6.29 (d, 1H), 6.15 (d, 1H), 6.08 (d, 1H), 2.18 (s, 3H)

Figure 3:
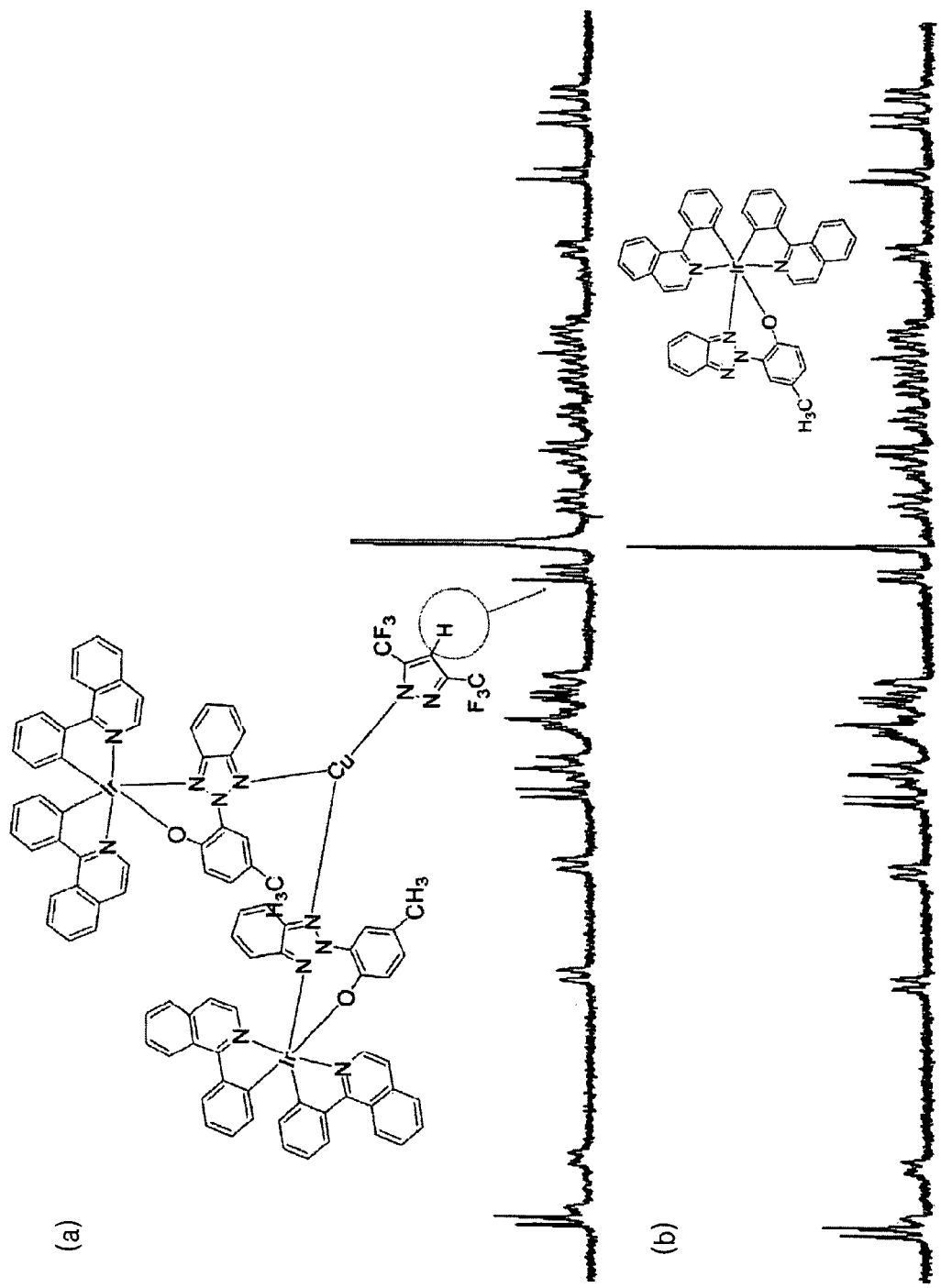
FIG. 3 is the NMR spectra of a copper(I)-iridium (III) complex (a) obtained in Example 1 and Ir(PIQ)$_2$OBT(bis-[N, C-2-phenylisoquinoliato](2-hydroxy-5methyl-phenyl) benzo-1,2,5-triazolato iridium(III) (b)

The structure of the final product was analyzed and identified through $^1$H NMR spectroscopy. The result is shown in FIG. 3. In FIG. 3, (a) is the NMR spectrum of the copper (I)-iridium (III) complex of Formula 6, and (b) is the NMR spectrum of IrPIQOBT. The two NMR spectra differ in that whether di(trifluoromethyl)pyrazole is bound or not.

The photoluminescence of the compound of Formula 6 obtained through the above-described processes was measured using a 10-$^4$ M solution of the compound of Formula 6 dissolved in methylene chloride. In addition, the compound of Formula 6 was spin-coated on a neat film to measure the photoluminescence of the compound of Formula 6 in film form.

Figure 4:
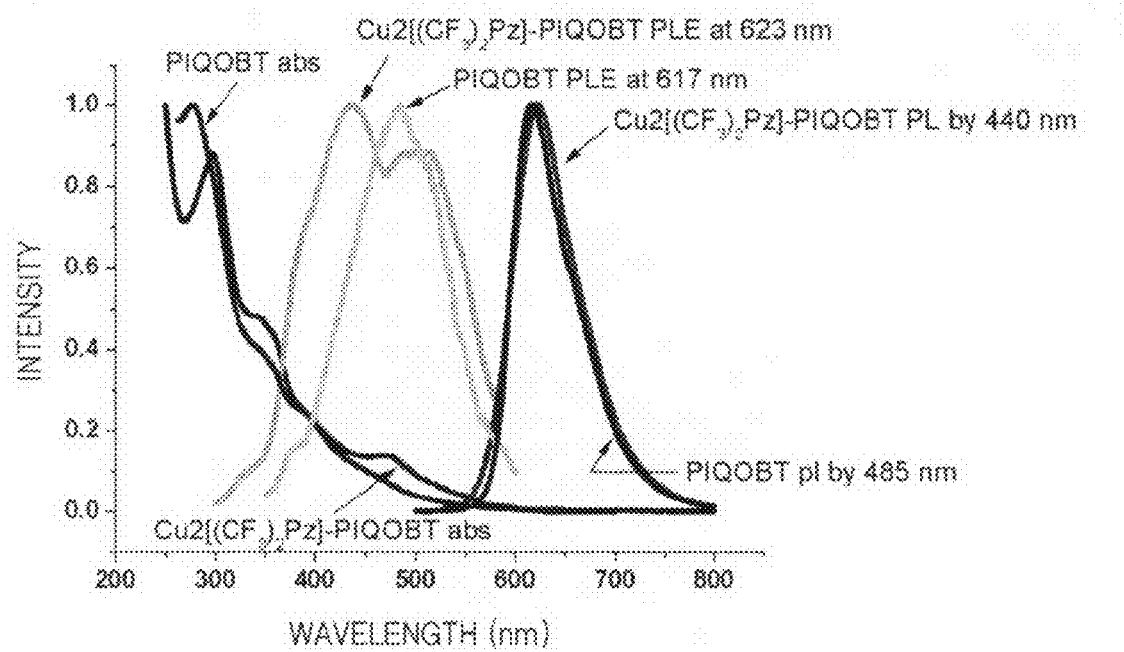
FIG. 4 is the PL spectrum of the compound of the copper (I)-iridium (III) complex obtained in Example 1.

The photoluminescence (PL) and color coordinates (CIE) of the compound of Formula 6 obtained in Example 1 are summarized in Table 1. The PL of the compound of Formula 6 is also illustrated in FIG. 4.

TABLE 1

| Example | PL λ_max (nm) Solution | Film | CIE (x, y) Solution | Film |
|---|---|---|---|---|
| Example 1: | 623 | 630 | (0.64, 0.35) | (0.65, 0.33) |

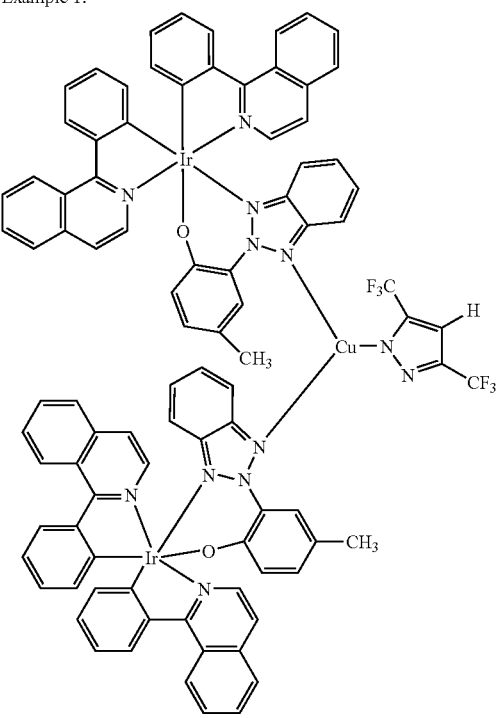

Due to the excellent electron transporting ability of pyrazole, the presence of the bridging (2-hydroxy-5methyl-phenyl)benzo-1,2,5-triazolate ligand that coordinates both Ir(III) in the Ir(piq)$_2$ moiety and a copper atom, and a substituted heteroaromatic ring coordinated to an iridium metal atom, red light can be effectively emitted. As is apparent from Table 1, the copper (I)-iridium (III) complex according to an embodiment of the present invention can produce dopants having excellent phosphorescent characteristics, and is suitable as a phosphorescent material emitting light in a red wavelength region (590-630 nm).

EXAMPLE 2

Manufacture of Organic EL Device

An indium-tin oxide (ITO)-coated transparent electrode substrate was washed, and an ITO electrode pattern was formed by patterning the ITO layer using a photoresist resin and an etchant and washed. PEDOT{poly(3,4-ethylenedioxythiophene)}[CH-8000] was coated on the washed structure to a thickness of about 50 nm and baked at 120° C. for about 5 minutes to form a hole injecting layer.

A solution of 8% dopants and hosts (mHost5:PBD:TPD=12:8:3) dissolved in chloroform was spin-coated on the hole injecting layer and baked at 100° C. for 1 hour. The solvent was completely removed from the coated layer in a vacuum oven to form an emitting layer having a thickness of 50 nm. Next, TPBI was vacuum-deposited on the emitting layer using a vacuum deposition apparatus under a pressure of $4\times10^{-6}$ torr or less to form an electron transporting layer having a thickness of 45 nm. Next, LiF was vacuum-deposited on the electron transporting layer at a rate of 0.1 Å/sec to form an electron injecting layer having a thickness of 0.8 nm.

Subsequently, Al was deposited at a rate of 10 Å/sec to form a cathode having a thickness of 200 nm. Finally, the resulting structure was encapsulated, thereby resulting in an organic EL device. Here, the encapsulating process was performed by putting BaO powder into a metal can, forming a sealant on the edge of the substrate, and sealing the metal can using a UV hardener in a glove box under a dry nitrogen gas to encapsulate the structure.

Figure 2:
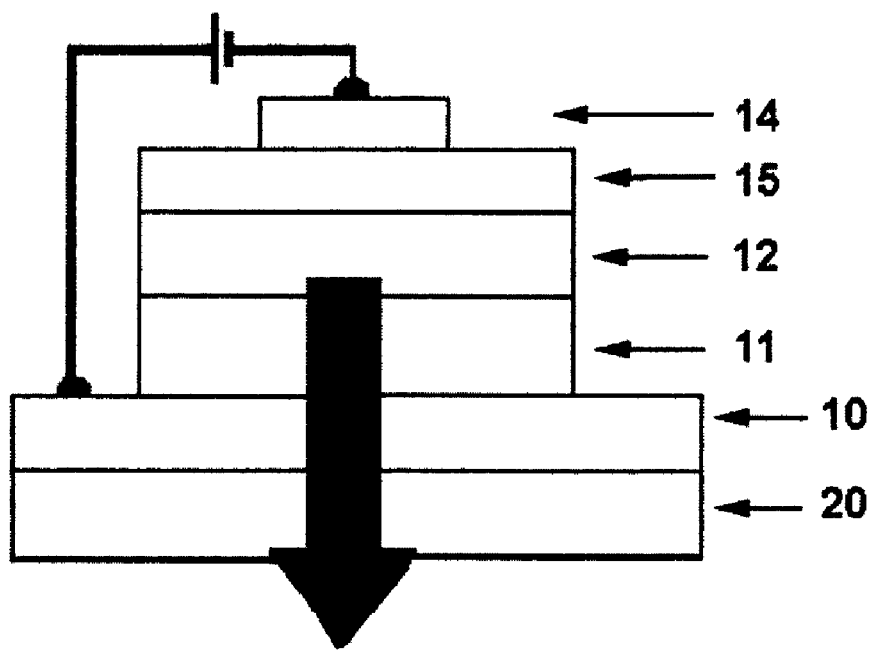
FIG. 2 is a diagram illustrating an organic EL device according to an embodiment of the present invention.

The organic EL device had a multi-layered structure as illustrated in FIG. 2, and a light emission area of 6 mm$^2$.

The electroluminescence characteristics, color coordinates (CIE), luminance efficiency, turn-on voltage, and brightness of the organic EL device manufactured in Example 2 are shown in Table 2.

TABLE 2

| | EL λ_max (nm) | CIE (x, y) | Luminance efficiency (Cd/A) | Turn-on voltage (V) | Maximum brightness (cd/m$^2$) |
|---|---|---|---|---|---|
| Example 2 | 623 | (0.64, 0.34) | 7.6 at 5.5 V | 3.5 | 1129 at 10 V |

As is apparent from Table 2, the organic EL device of Example 2 containing the compound synthesized in Example 1 according to an embodiment of the present invention has a high brightness in a red wavelength region, can operate at a low voltage, and has a high luminance efficiency at a low voltage.

Figure 5:
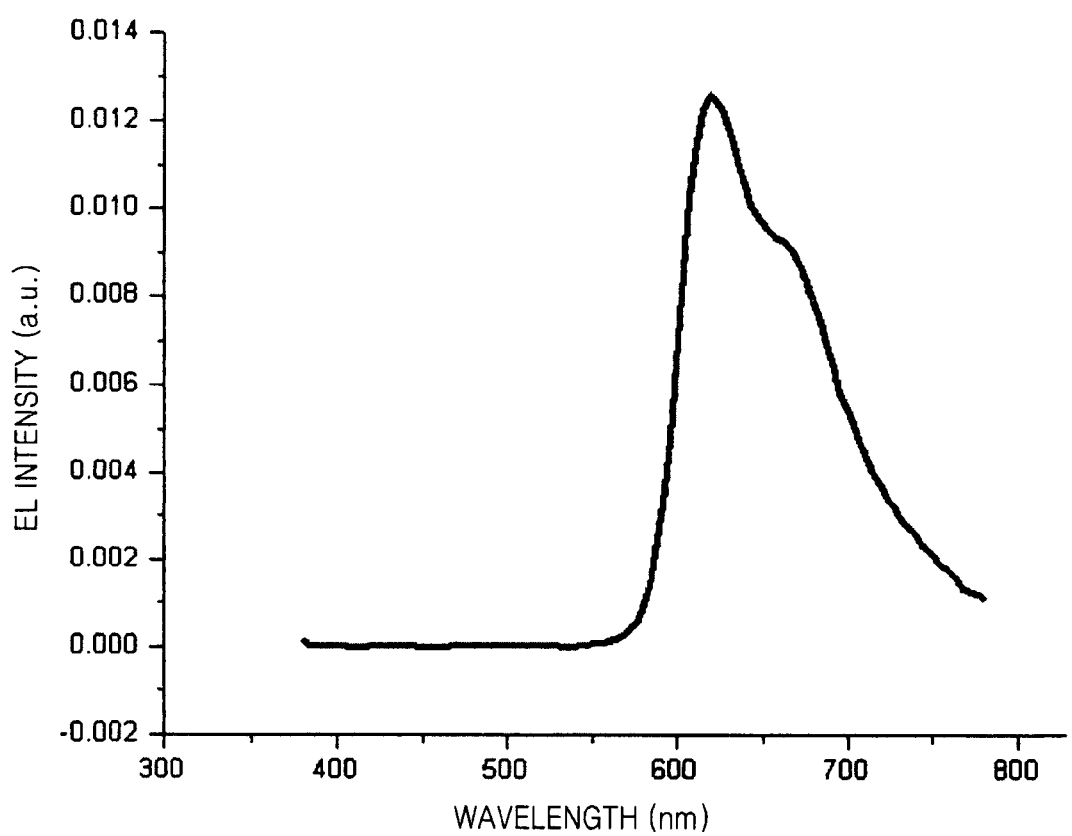
FIG. 5 is the EL spectrum of an organic EL device using the copper (I)-iridium (III) complex obtained in the Example 1.

A change in electroluminescence intensity of the organic EL device manufactured in Example 2 with respect to wavelength is illustrated in FIG. 5. When the compound synthesized in Example 1 according to an embodiment of the present invention is used as dopants, there are improvements in all the characteristics described above.

EXAMPLE 3

Synthesis of Compound of Formula 7

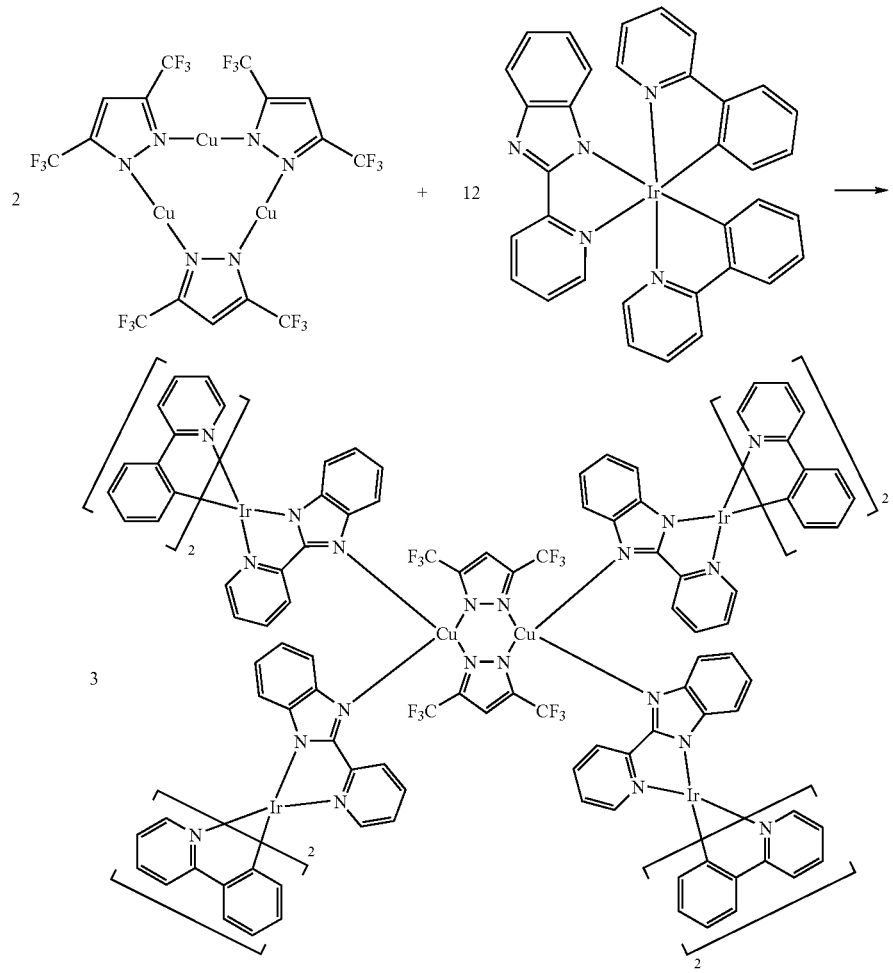

0.84 g (1.2 mmole) of IrPPYPYB (bis-[N,C'-2-phenylpyridinato](2-pyridyl)benzimidazolato Iridium (III)) and 0.16 g (0.2 mmole) of [(3,5-trifluoromethylpyrazolato)Cu]$_3$ [(3,5-(CF$_3$)$_2$Pz)-Cu]$_3$ were added to 20-30 mL of benzene and reacted at room temperature for 12-16 hours. The solvent was evaporated from the reaction product. A resulting green solid product was recrystallized using a mixture of benzene and hexane. The compound emits green light.

EXAMPLE 4

Synthesis of Compound of Formula 9

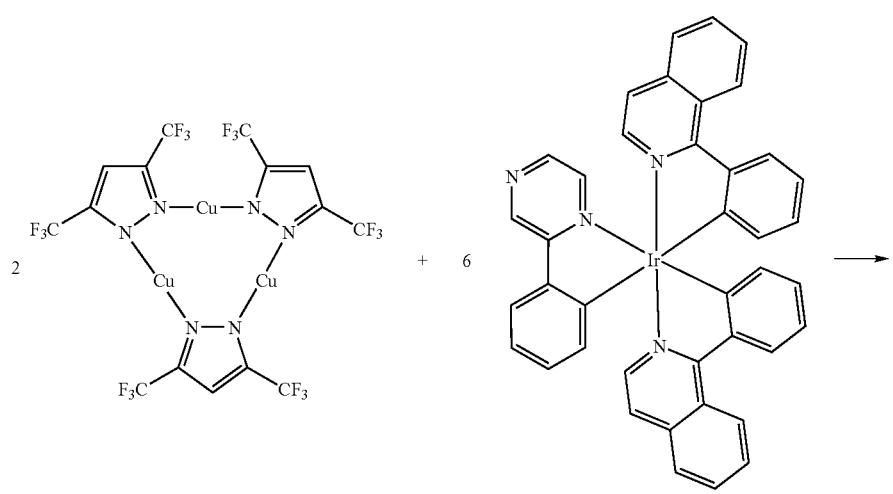

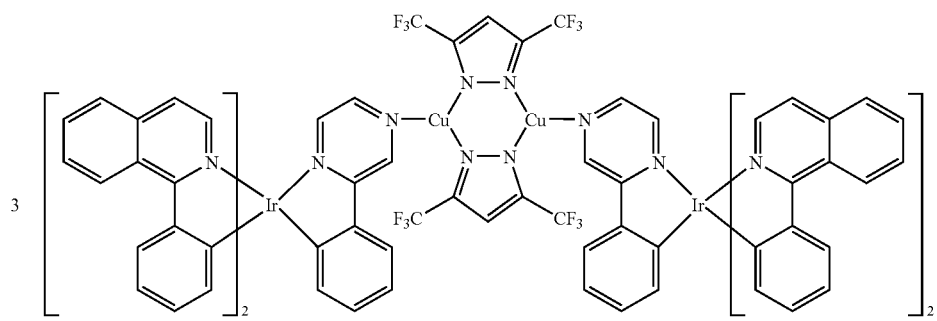

0.46 g (0.6 mmole) of IrPIQPZP (bis-[N,C'-2-phenylquinolinato](2-phenyl)pyrazolato Iridium (III)) and 0.16 g (0.2 mmole) of [(3,5-trifluoromethylpyrazolato)Cu]$_3$ [(3,5-(CF$_3$)$_2$Pz)-Cu]$_3$ were added to 20-30 mL of benzene and reacted at room temperature for 12-16 hours. The solvent was evaporated from the reaction product. A resulting red solid product was recrystallized using a mixture of benzene and hexane. The compound emits red light.

A heteronuclear copper (I)-iridium (III) complex according to an embodiment of the present invention can efficiently emit light in a red wavelength region (590-630 nm). The copper (I)-iridium (III) complex can be used to form an organic layer of an organic EL device and can emit light in a wavelength region of 590-630 nm as a high-efficient phosphorescent material. The copper (I)-iridium (III) complex can emit white light when used together with a green luminescent material or a blue luminescent material.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A heteronuclear copper (I)-iridium (III) complex represented by a formula selected from the group consisting of Formulae 1 through 3:

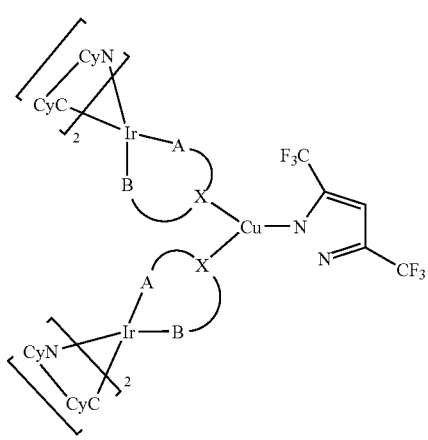

(1)

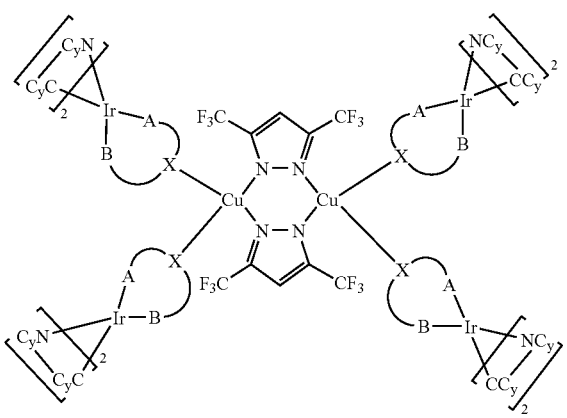

(2)

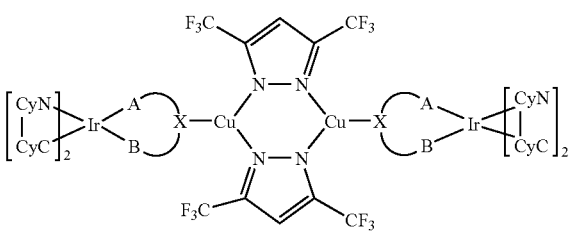

(3)

where A-X—B is a mononegative bidentate auxiliary ligand containing a hetero atom X;

X is N, P, S, or O;

CyN is 1,2,4-triazole, a substituted or unsubstituted C$_3$-C$_{60}$ hetero ring group including nitrogen bound to iridium (III), or a substituted or unsubstituted C$_3$-C$_{60}$ heteroaryl group including nitrogen bound to iridium;

CyC is a substituted or unsubstituted C$_4$-C$_{60}$ cyclic group including carbon bound to iridium, a substituted or unsubstituted C$_3$-C$_{60}$ hetero ring group including carbon bound to iridium, a substituted or unsubstituted C$_6$-C$_{60}$ aryl group including carbon bound to iridium, or a substituted or unsubstituted C$_3$-C$_{60}$ heteroaryl group including carbon bound to iridium; and CyN-CyC is a cyclometalating ligand coordinated to iridium via the nitrogen of the CyN and the carbon of the CyC, and, alternative to the above definition of CyN and CyC, CyN-CyC is optionally

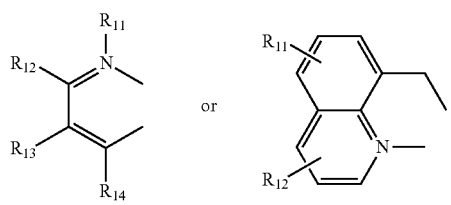

Where $R_{11}$, $R_{12}$, $R_{13}$ and $R_{14}$ are each independently selected from the group consisting of hydrogen, a halogen atom, —OR, —N(R)$_2$, —P(R)$_2$, —POR, —PO$_2$R, —PO$_3$R, —SR, —Si(R)$_3$, —B(R)$_2$, —B(OR)$_2$, —C(O)R, —C(O)OR, —C(O)N(R), —CN, —NO$_2$, —SO$_2$, —SOR, —SO$_2$R, —SO$_3$R, a $C_1$-$C_{20}$ alkyl group, and a $C_6$-$C_{20}$ aryl group, wherein R is selected from the group consisting of hydrogen, a halogen atom, a substituted or unsubstituted $C_1$-$C_{20}$ alkyl group, a substituted or unsubstituted $C_1$-$C_{10}$ alkoxy group, a substituted or unsubstituted $C_2$-$C_{20}$ alkenyl group, a substituted or unsubstituted $C_2$-$C_{20}$ alkenyl group, a substituted or unsubstituted $C_1$-$C_{20}$ heteroalkyl, a substituted or unsubstituted $C_6$-$C_{40}$ aryl group, a substituted or unsubstituted $C_7$-$C_{40}$ arylalkyl group, a substituted or unsubstituted $C_7$-$C_{40}$ alkylaryl group, a substituted or unsubstituted $C_2$-$C_{40}$ heteroaryl group, and a substituted or unsubstituted $C_3$-$C_{40}$ heteroarylalkyl group.

2. The heteronuclear copper(I)-iridium(III) complex of claim 1, wherein the cyclometalating ligand CyN-CyC is represented by one of the formulae:

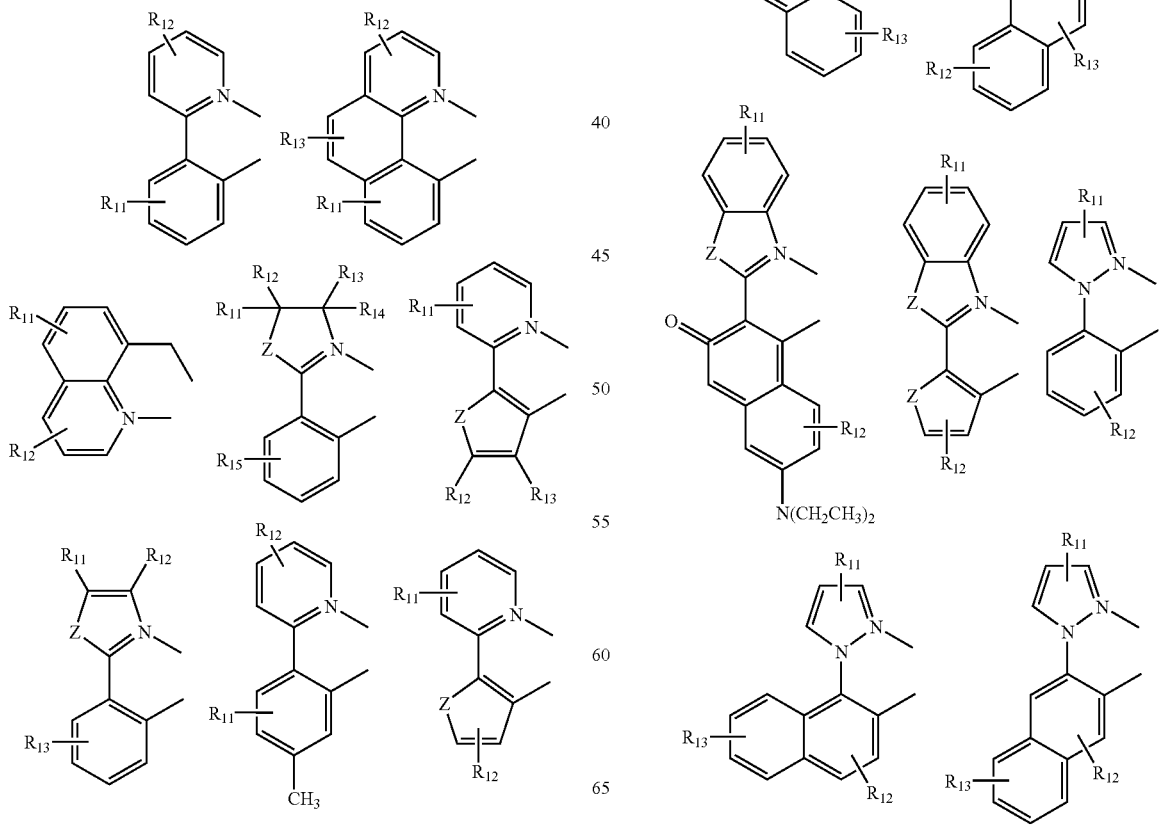
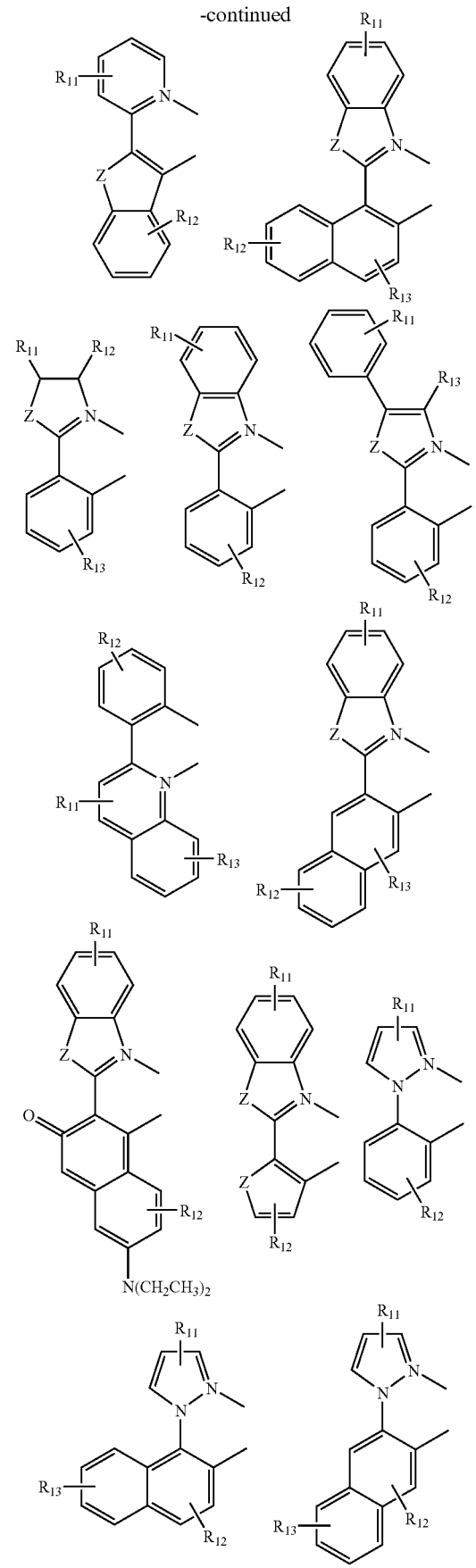

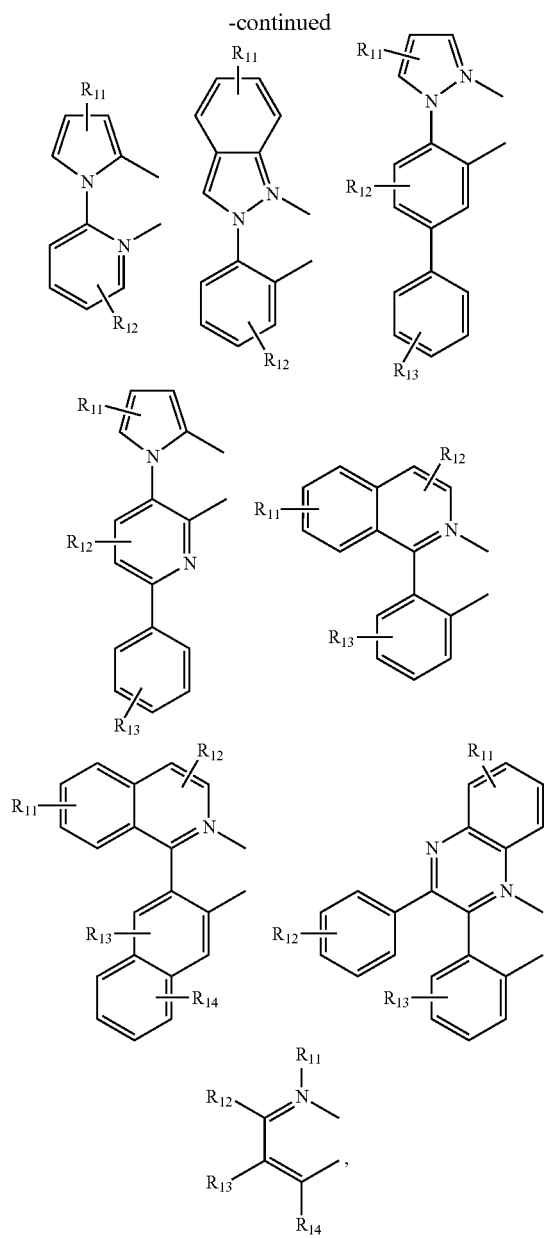

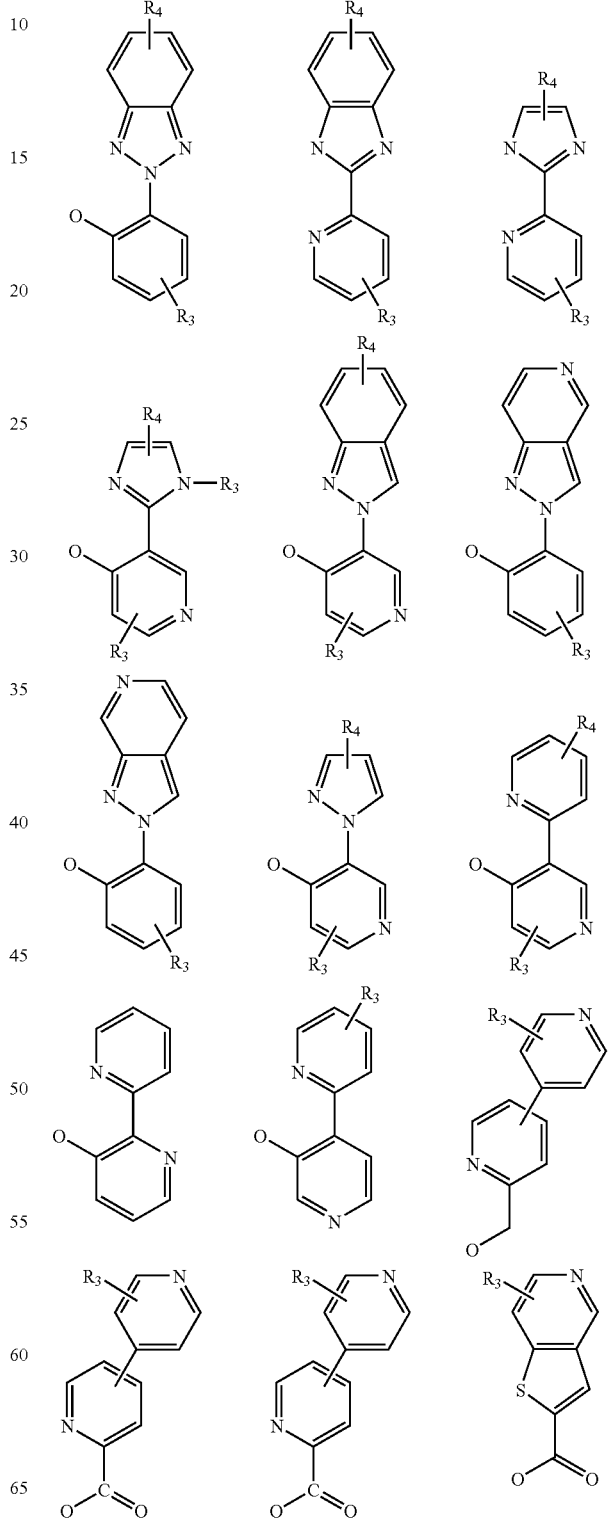

where the cyclometalating ligand CyN-CyC is mono-substituted or multi-substituted with at least one of $R_{11}$, $R_{12}$, $R_{13}$, $R_{14}$, and $R_{15}$, and $R_{11}$, $R_{12}$, $R_{13}$, $R_{14}$, and $R_{15}$ are each independently selected from the group consisting of hydrogen, a halogen atom, —OR, —N(R)$_2$, —P(R)$_2$, —POR, —PO$_2$R, —PO3R, —SR, —Si(R)$_3$, —B(R)$_2$, —B(OR)$_2$, —C(O)R, —C(O)OR, —C(O)N(R), —CN, —NO$_2$, —SO$_2$, —SOR, —SO$_2$R, —SO$_3$R, a $C_1$-$C_{20}$ alkyl group, and a $C_6$-$C_{20}$ aryl group;

R is selected from the group consisting of hydrogen, a halogen atom, a substituted or unsubstituted $C_1$-$C_{20}$ alkyl group, a substituted or unsubstituted $C_1$-$C_{10}$ alkoxy group, a substituted or unsubstituted $C_2$-$C_{20}$ alkenyl group, a substituted or unsubstituted $C_2$-$C_{20}$ alkynyl group, a substituted or unsubstituted $C_1$-$C_{20}$ heteroalkyl, a substituted or unsubstituted $C_6$-$C_{40}$ aryl group, a substituted or unsubstituted $C_7$-$C_{40}$ arylalkyl group, a substituted or unsubstituted $C_7$-$C_{40}$ alkylaryl group, a substituted or unsubstituted $C_2$-$C_{40}$ heteroaryl group, and a substituted or unsubstituted $C_3$-$C_{40}$ heteroarylalkyl group; and Z is S, O, or NR$_0$ where R$_0$ is hydrogen or a $C_1$-$C_{20}$ alkyl group.

3. The heteronuclear copper(I)-iridium(III) complex of claim 1, wherein the ligand A-X—B is represented by one of the formulae below:

-continued

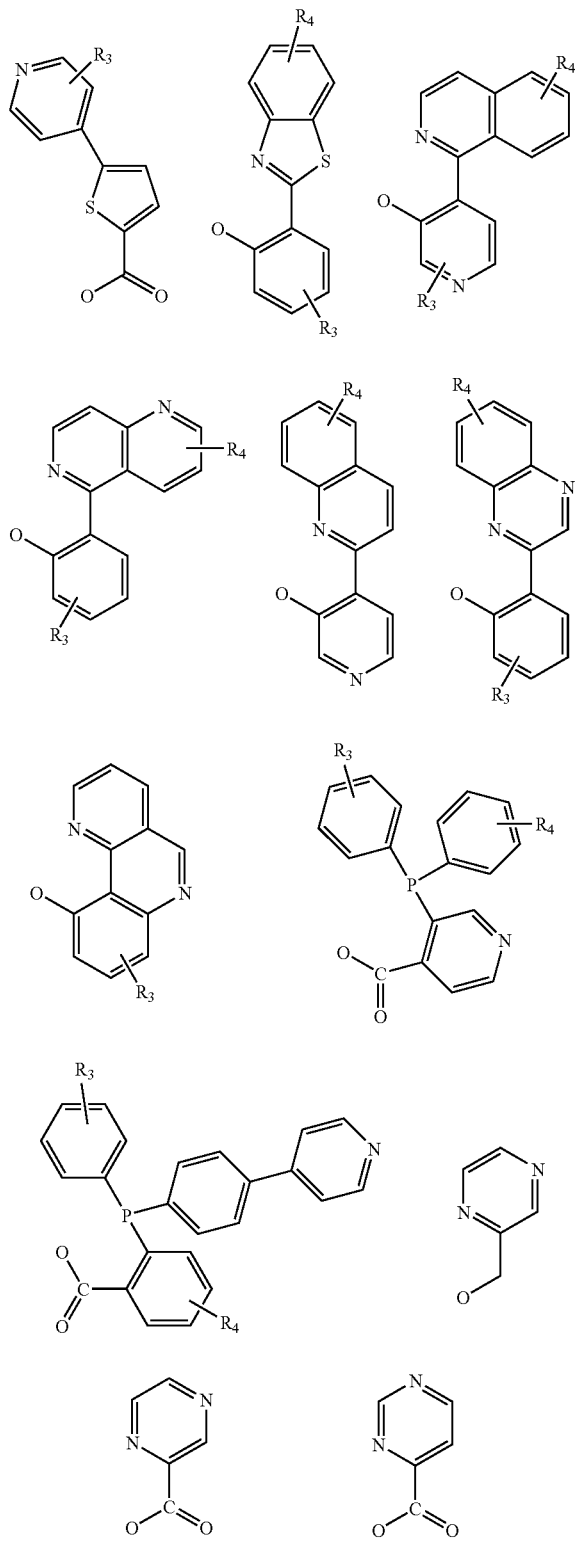

where the ligands A-X—B are mono-substituted or multi-substituted with at least one of $R_1$, $R_2$, $R_3$, and $R_4$, and $R_1$, $R_2$, $R_3$, and $R_4$ are each independently selected from the group consisting of hydrogen, a halogen atom, —OR, —N(R)$_2$, —P(R)$_2$, —POR, —PO$_2$R, —PO$_3$R, —SR, —Si(R)$_3$, —B(R)$_2$, —B(OR)$_2$, —C(O)R, —C(O)OR, —C(O)N(R), —CN, —NO$_2$, —SO$_2$, —SOR, —SO$_2$R, —SO$_3$R, a $C_1$-$C_{20}$ alkyl group, and a $C_6$-$C_{20}$ aryl group; and R is selected from the group consisting of hydrogen, a halogen atom, a substituted or unsubstituted $C_1$-$C_{20}$ alkyl group, a substituted or unsubstituted $C_1$-$C_{10}$ alkoxy group, a substituted or unsubstituted $C_2$-$C_{20}$ alkenyl group, a substituted or unsubstituted $C_2$-$C_{20}$ alkynyl group, a substituted or unsubstituted $C_1$-$C_{20}$ heteroalkyl, a substituted or unsubstituted $C_6$-$C_{40}$ aryl group, a substituted or unsubstituted $C_7$-$C_{40}$ arylalkyl group, a substituted or unsubstituted $C_7$-$C_{40}$ alkylaryl group, a substituted or unsubstituted $C_2$-$C_{40}$ heteroaryl group, and a substituted or unsubstituted $C_3$-$C_{40}$ heteroarylalkyl group.

4. The heteronuclear copper(I)-iridium(III) complex of claim 1, wherein CyN is selected from the group consisting of pyrrolidine, morpholine, thiomorpholine, thiazolidine, pyridine, 4-methoxypyridine, quinoline, pyrrole, indole, pyrazine, pyrazole, imidazole, pyrimidine, quinazoline, thiazole, oxazole, triazine, and 1,2,4-triazole;

CyC is selected from the group consisting of cyclohexane, cyclopentane, tetrahydrofuran, 1,3-dioxane, 1,3-dithiane, 1,3-dithiolane, 1,4-dioxa-8-azaspiro[4,5]decane, 1,4-dioxaspiro[4,5]decan-2-one, phenyl, 1,3-benzodioxole, biphenyl, naphthalene, anthracene, azulene, thiophene, furan2(5H)-furanone, pyridine, coumarin, imidazole, 2-phenylpyridine, 2-benzothiazole, 2-benzooxazole, 1-phenylpyrazole, 1-naphthylpyrazole,5-(4-methoxyphenyl) pyrazole, 2,5-bisphenyl-1,3,4-oxadiazole, 2,3-benzofuran, and 2-(4-biphenyl)-6-phenyl benzooxazole; and A and B are independently selected from the group consisting of cyclohexyl, cyclopentyl, cyclooctyl, phenyl, 1,3-benzodioxole, biphenyl, naphthalene, anthracene, azulene, thiophene, furan2(5H)-furanone, pyridine, coumarin, imidazole, 2-phenylpyridine, 2-benzothiazole, 2-benzooxazole, 1-phenylpyrazole, 1-naphthylpyrazole, 5-(4-methoxyphenyl)pyrazole, 2, 5-bisphenyl-1,3,4-oxadiazole, 2,3-benzofuran and 2-(4-biphenyl)-6-phenyl benzooxazole.

5. An organic electroluminescent device comprising an organic layer between a pair of electrodes, the organic layer containing the copper(I)-iridium (III) complex of claim 1.

6. The organic electroluminescent device of claim 5, wherein the organic layer is an emitting layer.

7. The organic electroluminescent device of claim 6, wherein the amount of the copper (I)-iridium (III) complex is in a range of 1-30 parts by weight based on 100 parts by the total weight of the emitting layer.

8. The organic electroluminescent device of claim 5, wherein the organic layer further comprises at least one host selected from the group consisting of a polymer host, a mixed host of a polymer and a low-molecular weight material, a low-molecular weight host, and a non-emitting polymer matrix.

9. The organic electroluminescent device of claim 5, wherein the organic layer further comprises one of a green luminescent material and a blue luminescent material.

10. A heteronuclear copper (I)-iridium (III) complex represented by Formula 1:

(1)

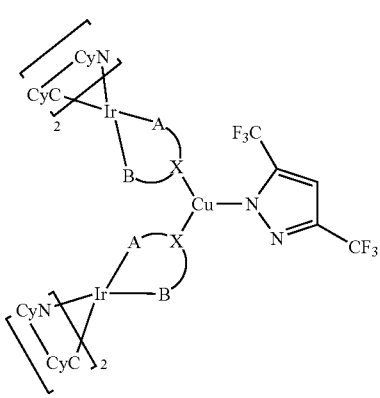

where A-X—B is a mononegative bidentate auxiliary ligand containing a hetero atom X;

X is N, P, S, or O;

CyN is a substituted or unsubstituted $C_3$-$C_{60}$ hetero ring group including nitrogen bound to iridium (III), or a substituted or unsubstituted $C_3$-$C_{60}$ heteroaryl group including nitrogen bound to iridium;

CyC is a substituted or unsubstituted $C_4$-$C_{60}$ cyclic group including carbon bound to iridium, a substituted or unsubstituted $C_3$-$C_{60}$ hetero ring group including carbon bound to iridium, a substituted or unsubstituted $C_6$-$C_{60}$ aryl group including carbon bound to iridium, or a substituted or unsubstituted $C_3$-$C_{60}$ heteroaryl group including carbon bound to iridium; and CyN-CyC indicates a cyclometalating ligand coordinated to iridium via the nitrogen of the CyN and the carbon of the CyC.

11. The heteronuclear copper(I)-iridium(III) complex of claim 10, being a compound represented by Formula 6:

(6)

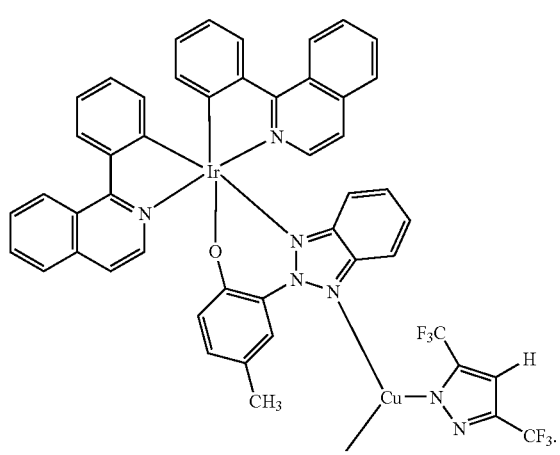

12. A heteronuclear copper(I)-iridium(III) complex represented by Formula 2:

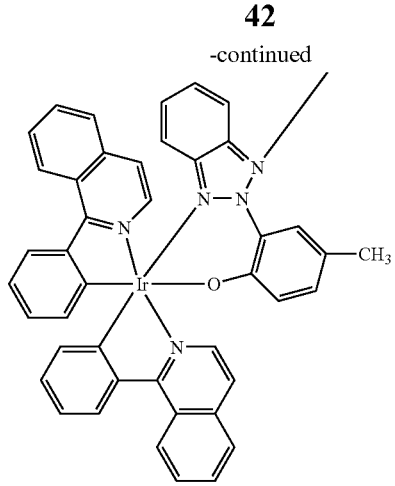

(2)

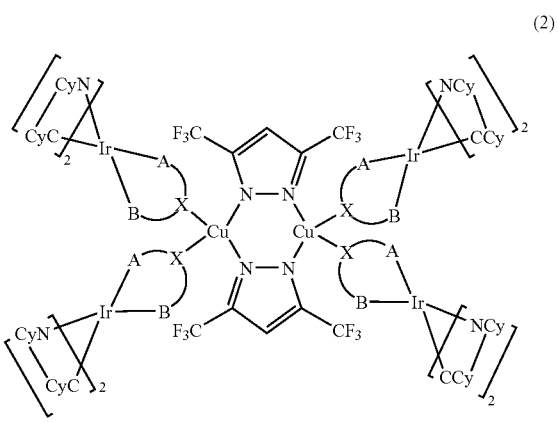

where A-X—B is a mononegative bidentate auxiliary ligand containing a hetero atom X;

X is N, P, S, or O;

CyN is a substituted or unsubstituted $C_3$-$C_{60}$ hetero ring group including nitrogen bound to iridium (III), or a substituted or unsubstituted $C_3$-$C_{60}$ heteroaryl group including nitrogen bound to iridium;

CyC is a substituted or unsubstituted $C_4$-$C_{60}$ cyclic group including carbon bound to iridium, a substituted or unsubstituted $C_3$-$C_{60}$ hetero ring group including carbon bound to iridium, a substituted or unsubstituted $C_6$-$C_{60}$ aryl group including carbon bound to iridium, or a substituted or unsubstituted $C_3$-$C_{60}$ heteroaryl group including carbon bound to iridium; and CyN-CyC indicates a cyclometalating ligand coordinated to iridium via the nitrogen of the CyN and the carbon of the CyC.

13. The heteronuclear copper(I)-iridium(III) complex of claim 12, being a compound represented by one of Formulae 7 and 8:

(7)
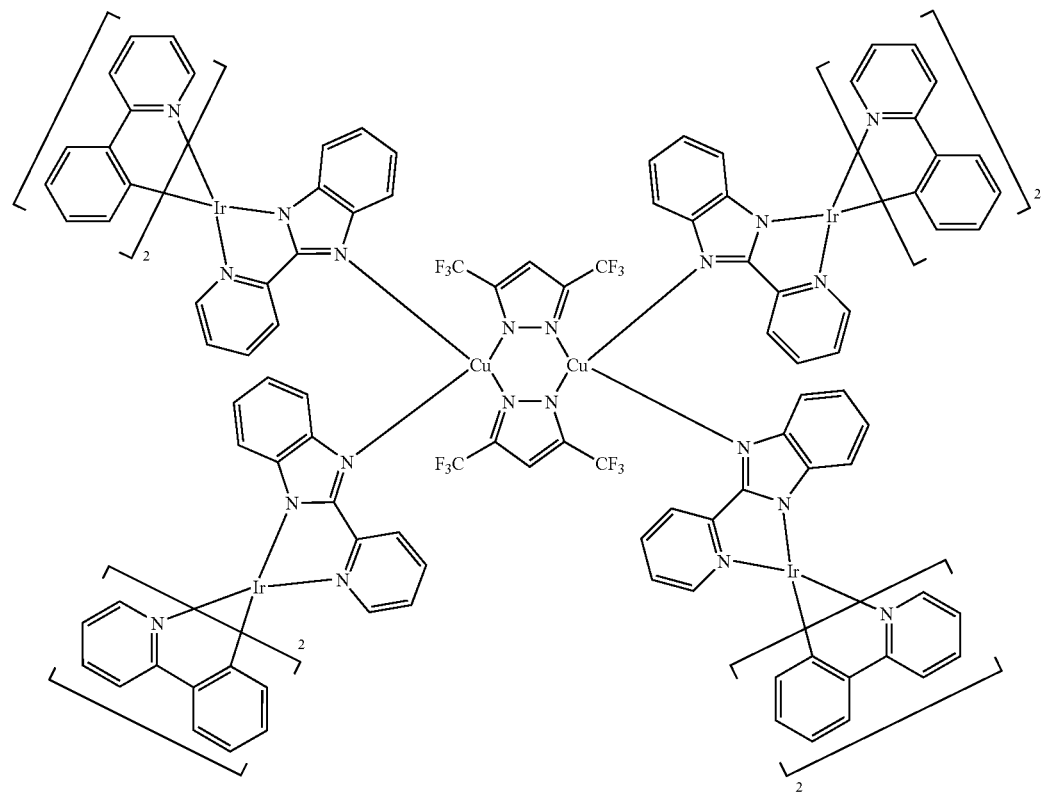
(8)
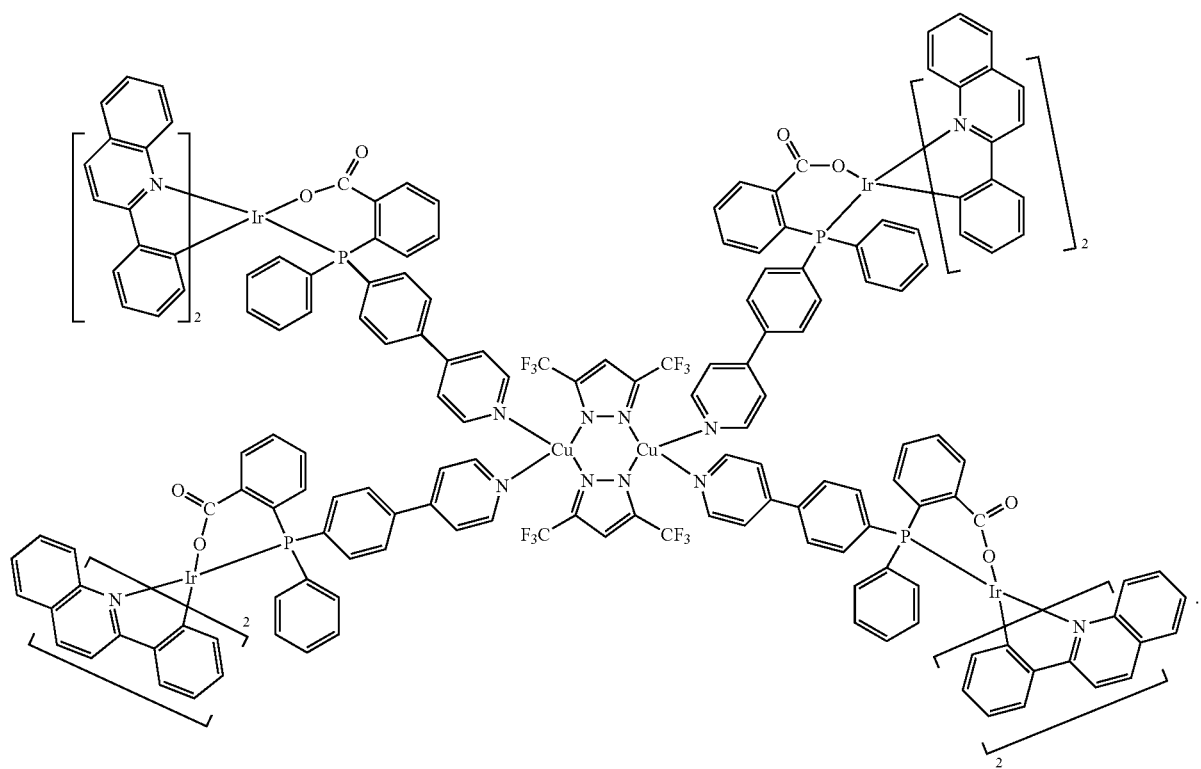

14. A heteronuclear copper(I)-iridium(III) complex represented by Formula 3:

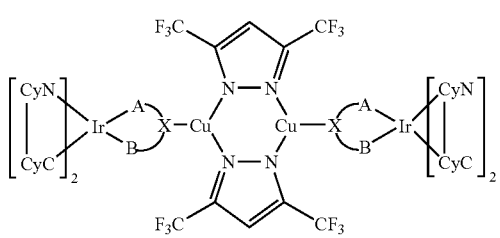

(3)

where A-X—B is a mononegative bidentate auxiliary ligand containing a hetero atom X;

X is N, P, S, or O;

CyN is a substituted or unsubstituted $C_3$-$C_{60}$ hetero ring group including nitrogen bound to iridium (III), or a substituted or unsubstituted $C_3$-$C_{60}$ heteroaryl group including nitrogen bound to iridium;

CyC is a substituted or unsubstituted $C_4$-$C_{60}$ cyclic group including carbon bound to iridium, a substituted or unsubstituted $C_3$-$C_{60}$ hetero ring group including carbon bound to iridium, a substituted or unsubstituted $C_6$-$C_{60}$ aryl group including carbon bound to iridium, or a substituted or unsubstituted $C_3$-$C_{60}$ heteroaryl group including carbon bound to iridium; and CyN-CyC indicates a cyclometalating ligand coordinated to iridium via the nitrogen of the CyN and the carbon of the CyC.

15. The heteronuclear copper(I)-iridium(III) complex of claim 14, being a compound represented by Formula 4:

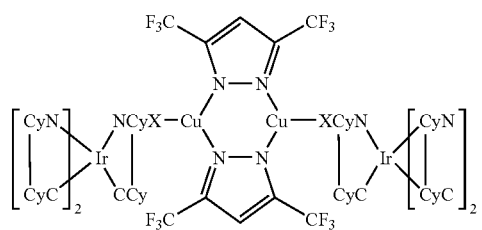

(4)

where X is N, P, S, or O;

CyN is a substituted or unsubstituted $C_3$-$C_{60}$ hetero ring group including nitrogen bound to iridium (III), or a substituted or unsubstituted $C_3$-$C_{60}$ heteroaryl group including nitrogen bound to iridium;

CyC is a substituted or unsubstituted $C_4$-$C_{60}$ cyclic group including carbon bound to iridium, a substituted or unsubstituted $C_3$-$C_{60}$ hetero ring group including carbon bound to iridium, a substituted or unsubstituted $C_6$-$C_{60}$ aryl group including carbon bound to iridium, or a substituted or unsubstituted $C_3$-$C_{60}$ heteroaryl group including carbon bound to iridium;

NCyX is a substituted or unsubstituted $C_3$-$C_{60}$ hetero ring group including nitrogen bound to iridium (III) and including hetero atom X or a substituted or unsubstituted $C_3$-$C_{60}$ heteroaryl group including nitrogen bound to iridium and including hetero atom X; and CyN-CyC and NCyX-CCy are cyclometalating ligands coordinated to iridium via the nitrogen of the CyN and the carbon of the CyC.

16. The heteronuclear copper(I)-iridium(III) complex of claim 15, wherein the NCyX-CCy is one of the groups represented by formulae:

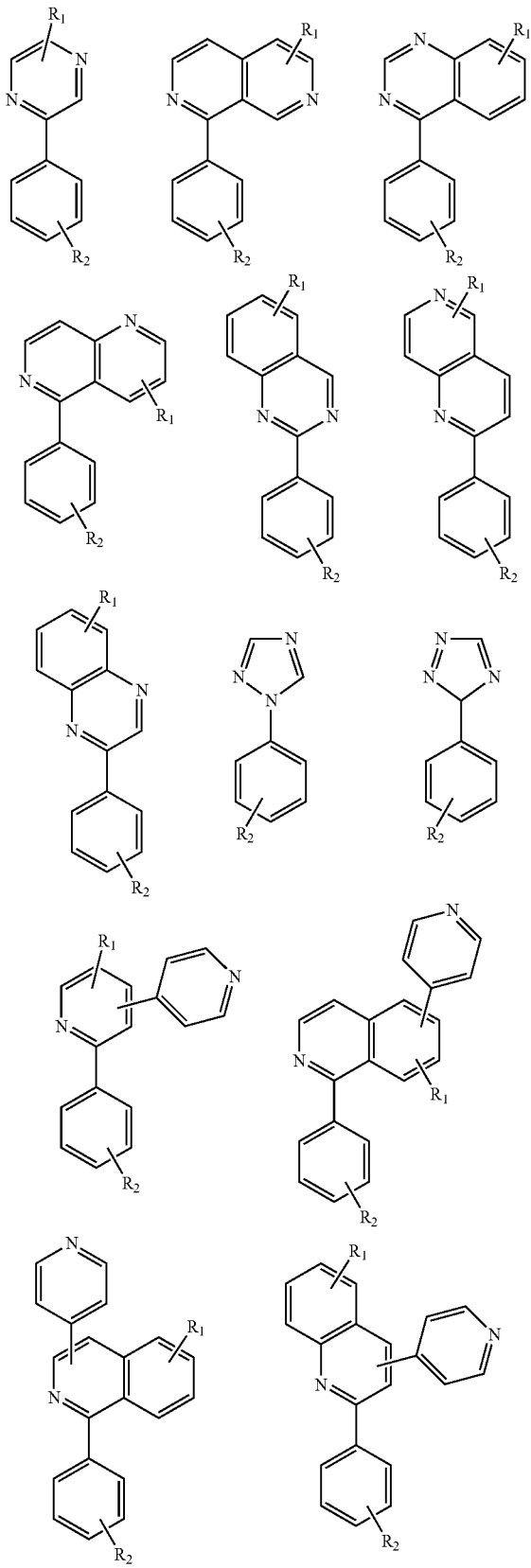

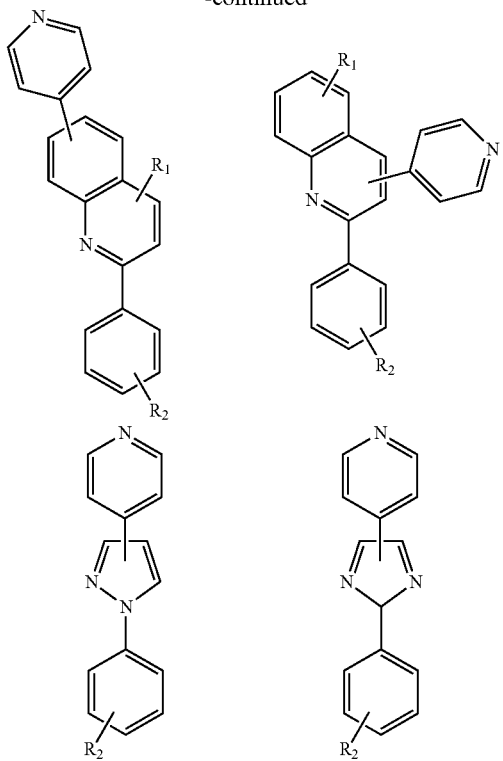

where the NCyX-CCy is mono-substituted or multi-substituted with at least one of $R_1$ and $R_2$, and $R_1$ and $R_2$ are each independently selected from the group consisting of hydrogen, a halogen atom, —OR, —N(R)$_2$, —P(R)$_2$, —POR, —PO$_2$R, —PO$_3$R, —SR, —Si(R)$_3$, —B(R)$_2$, —B(OR)$_2$, —C(O)R, —C(O)OR, —C(O)N(R), —CN, —NO$_2$, —SO$_2$, —SOR, —SO$_2$R, —SO$_3$R, a $C_1$-$C_{20}$ alkyl group, and a $C_6$-$C_{20}$ aryl group; and R is selected from the group consisting of hydrogen, a halogen atom, a substituted or unsubstituted $C_1$-$C_{20}$ alkyl group, a substituted or unsubstituted $C_1$-$C_{10}$ alkoxy group, a substituted or unsubstituted $C_2$-$C_{20}$ alkenyl group, a substituted or unsubstituted $C_2$-$C_{20}$ alkynyl group, a substituted or unsubstituted $C_1$-$C_{20}$ heteroalkyl, a substituted or unsubstituted $C_6$-$C_{40}$ aryl group, a substituted or unsubstituted $C_7$-$C_{40}$ arylalkyl group, a substituted or unsubstituted $C_7$-$C_{40}$ alkylaryl group, a substituted or unsubstituted $C_7$-$C_{40}$ heteroaryl group, and a substituted or unsubstituted $C_3$-$C_{40}$ heteroarylalkyl group.

17. The heteronuclear copper (I)-iridium(III) complex of claim 14, being a compound represented by Formula 5:

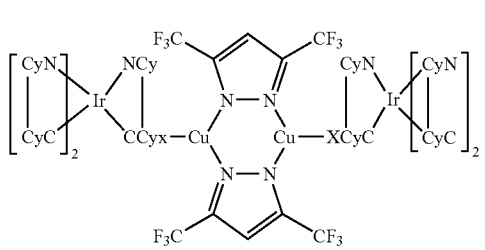

(5)

where X is N, P, S, or O;
CyN is a substituted or unsubstituted $C_3$-$C_{60}$ hetero ring group including nitrogen bound to iridium (III), or a substituted or unsubstituted $C_3$-$C_{60}$ heteroaryl group including nitrogen bound to iridium;

CyC is a substituted or unsubstituted $C_4$-$C_{60}$ cyclic group including carbon bound to iridium, a substituted or unsubstituted $C_3$-$C_{60}$ hetero ring group including carbon bound to iridium, a substituted or unsubstituted $C_6$-$C_{60}$ aryl group including carbon bound to iridium, or a substituted or unsubstituted $C_3$-$C_{60}$ heteroaryl group including carbon bound to iridium;

NCy is a substituted or unsubstituted $C_4$-$C_{60}$ cyclic group including nitrogen bound to iridium (III), a substituted or unsubstituted $C_3$-$C_{60}$ hetero ring group including nitrogen bound to iridium, a substituted or unsubstituted $C_3$-$C_{60}$ aryl group including nitrogen bound to iridium, or a substituted or unsubstituted $C_3$-$C_{60}$ heteroaryl group including nitrogen bound to iridium;

CCyX is a substituted or unsubstituted $C_3$-$C_{60}$ hetero ring group including carbon bound to iridium (III) and including hetero atom X or a substituted or unsubstituted $C_3$-$C_{60}$ heteroaryl group including carbon bound to iridium and including hetero atom X; and CyN-CyC and NCy-CCyX indicate cyclometalating ligands coordinated to iridium via the nitrogen of the CyN and the carbon of the CyC.

18. The heteronuclear copper(I)-iridium(III) complex of claim 16, wherein the NCy-CCyX is one of the groups represented by formulae below:

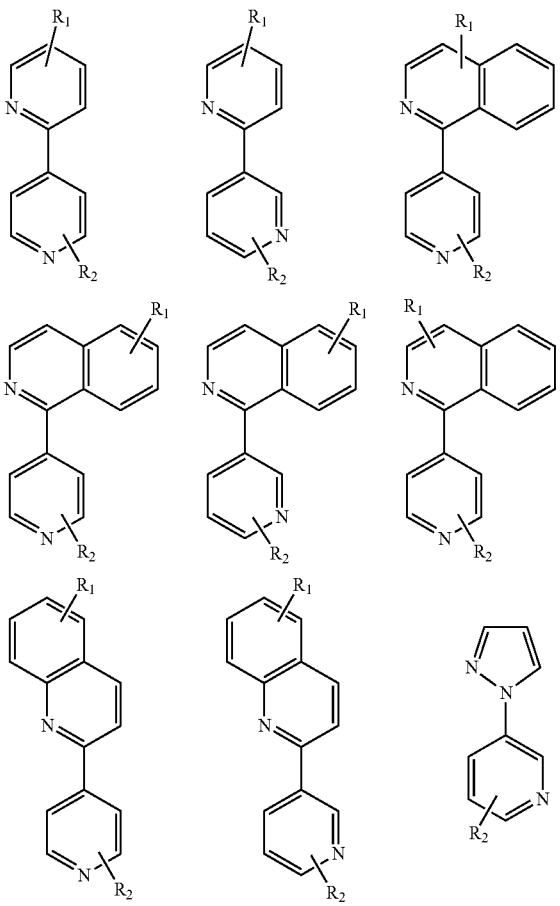

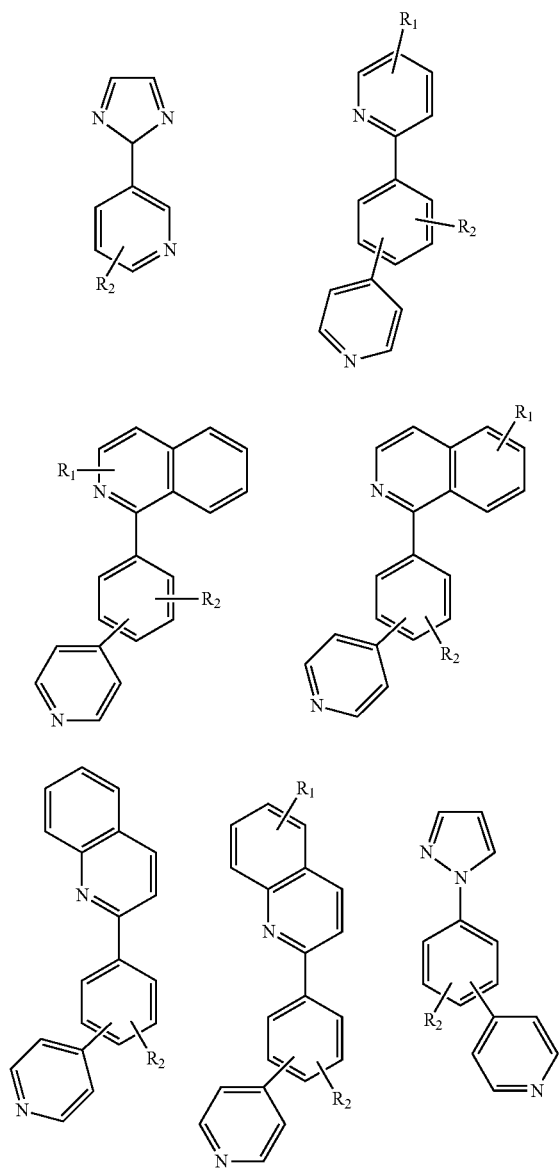

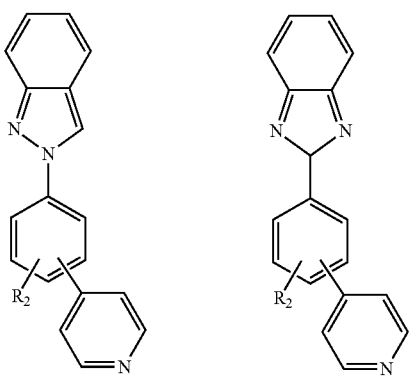

where the NCy-CCyX is mono-substituted or multi-substituted with at least one of $R_1$ and $R_2$, and $R_1$ and $R_2$ are each independently selected from the group consisting of hydrogen, a halogen atom, —OR, —N(R)$_2$, —P(R)$_2$, —POR, —PO$_2$R, —PO$_3$R, —SR, —Si(R)$_3$, —B(R)$_2$, —B(OR)$_2$, —C(O)R, —C(O)OR, —C(O)N(R), —CN, —NO$_2$, —SO$_2$, —SOR, —SO$_2$R, —SO$_3$R, a $C_1$-$C_{20}$ alkyl group, and a $C_6$-$C_{20}$ aryl group; and R is selected from the group consisting of hydrogen, a halogen atom, a substituted or unsubstituted $C_1$-$C_{20}$ alkyl group, a substituted or unsubstituted $C_1$-$C_{10}$ alkoxy group, a substituted or unsubstituted $C_2$-$C_{20}$ alkenyl group, a substituted or unsubstituted $C_2$-$C_{20}$ alkynyl group, a substituted or unsubstituted $C_1$-$C_{20}$ heteroalkyl, a substituted or unsubstituted $C_6$-$C_{40}$ aryl group, a substituted or unsubstituted $C_7$-$C_{40}$ arylalkyl group, a substituted or unsubstituted $C_7$-$C_{40}$ alkylaryl group, a substituted or unsubstituted $C_2$-$C_{40}$ heteroaryl group, and a substituted or unsubstituted $C_3$-$C_{40}$ heteroarylalkyl group.

19. The heteronuclear copper(I)-iridium(III) complex of claim 14, being a compound of one of Formulae 9 and 10:

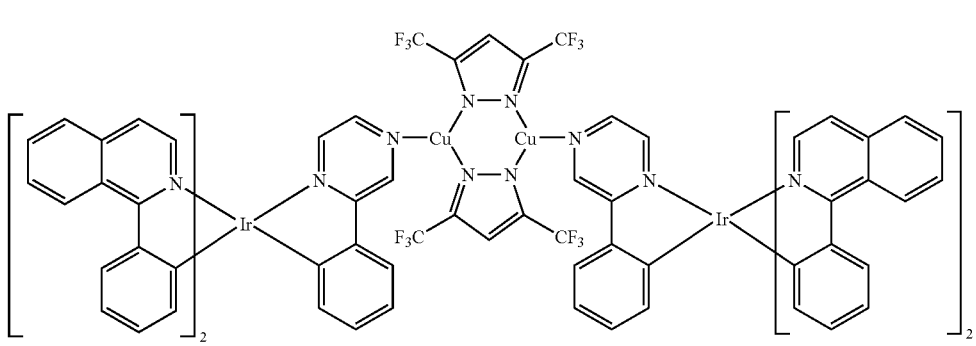

(9)

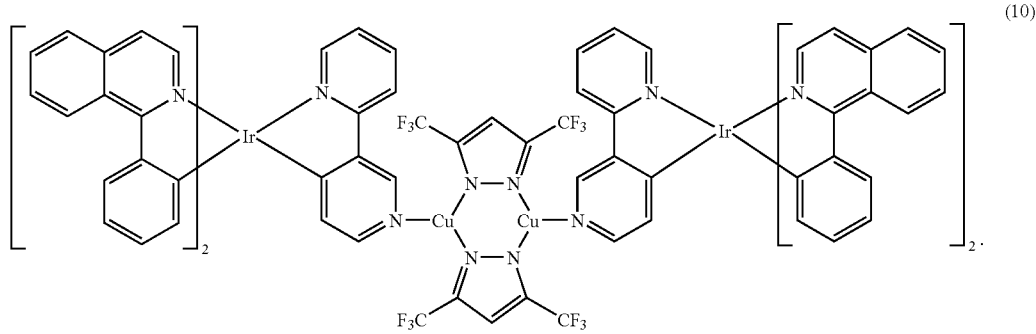
(10)

20. A method of preparing a copper (I)-iridium (III) complex represented by one selected from the group consisting of Formulae 1 through 3, the method comprising:

reacting a compound $[(3,5-(CF_3)_2Pz)-Cu]_3$ represented by Formula 11 with a compound of Formula 12:

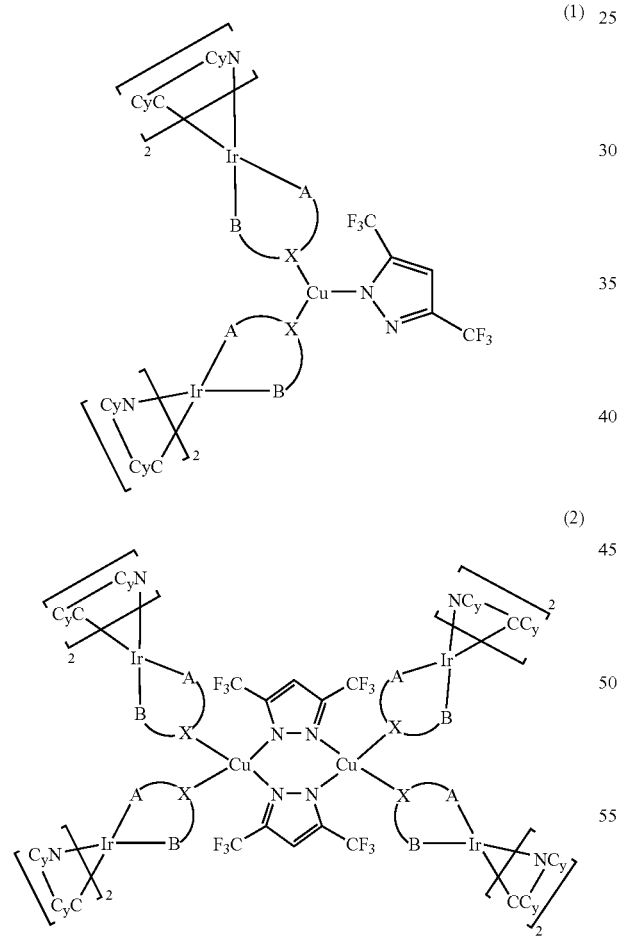

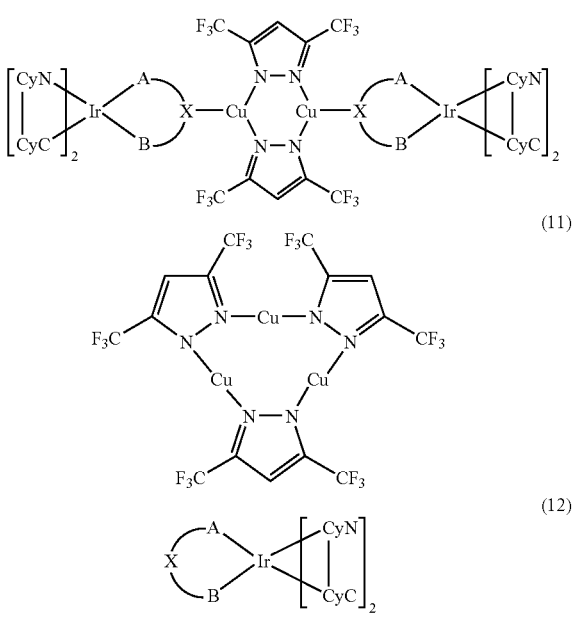

where A-X—B is a mononegative bidentate auxiliary ligand containing a hetero atom X;

X is N, P, S, or O;

CyN is a substituted or unsubstituted $C_3$-$C_{60}$ hetero ring group including nitrogen bound to iridium (III), or a substituted or unsubstituted $C_3$-$C_{60}$ heteroaryl group including nitrogen bound to iridium;

CyC is a substituted or unsubstituted $C_4$-$C_{60}$ cyclic group including carbon bound to iridium, a substituted or unsubstituted $C_3$-$C_{60}$ hetero ring group including carbon bound to iridium, a substituted or unsubstituted $C_6$-$C_{60}$ aryl group including carbon bound to iridium, or a substituted or unsubstituted $C_3$-$C_{60}$ heteroaryl group including carbon bound to iridium; and CyN-CyC indicates a cyclometalating ligand coordinated to iridium via the nitrogen of the CyN and the carbon of the CyC.

21. A copper (I)-iridium (III) complex prepared by the method of claim 20.

* * * * *